(12) United States Patent
Cerny et al.

(10) Patent No.: US 6,720,410 B2
(45) Date of Patent: Apr. 13, 2004

(54) NUCLEIC ACIDS ENCODING ENAMEL MATRIX RELATED POLYPEPTIDES

(75) Inventors: Radim Cerny, Plzen (CZ); Ivan Slaby, Huddinge (SE); Lars Hammarström, Djursholm (SE); Tilmann Wurtz, Tullinge (SE); Cheng Dan Fong, Huddinge (SE)

(73) Assignee: Biora AB, Malmo (SE)

( * ) Notice: Subject to any disclaimer, the term of this patent is extended or adjusted under 35 U.S.C. 154(b) by 222 days.

(21) Appl. No.: 09/950,739

(22) Filed: Sep. 13, 2001

(65) Prior Publication Data

US 2002/0106333 A1 Aug. 8, 2002

Related U.S. Application Data

(62) Division of application No. 08/732,749, filed on Oct. 18, 1996, now Pat. No. 6,300,062.
(60) Provisional application No. 60/005,634, filed on Oct. 19, 1995.

(51) Int. Cl.[7] .......................... C07H 21/04; C12P 21/06; C12N 1/21; C07K 14/00; A61K 31/70
(52) U.S. Cl. .................. 536/23.1; 435/69.1; 435/252.3; 435/320.1; 514/44; 530/388
(58) Field of Search .................. 536/23.1; 435/69.1, 435/70.1, 70.3, 71.2, 252.3, 320.1, 325; 514/44; 530/300, 350

(56) References Cited

FOREIGN PATENT DOCUMENTS

| | | |
|---|---|---|
| WO | 8908441 | 9/1989 |
| WO | WO 89/08441 * | 9/1989 |

OTHER PUBLICATIONS

Krebsbach et al. 271:4431–4435, 1996.*
Santoro, SA GenBank Accession # R28043, 1992.*
Gibson et al. Genbank Accession No: A37998, 1991.*
GenBank Sequence Listing Summaries of tetrapeptide matches.*
Matsuki, et al., *A Compliation of Partial Sequences of Randomly Selected cDNA Clones from Rat Incisor*, EMBL Database Entry RN973, Accession No.: R46973, 1995.
Matsuki, et al., *A Compliation of Partial Sequences of Randomly Selected cDNA Clones from Rat Incisor*, EMBL Database Entry RN992, Accession No.: R46992, 1995.

Cerny, et al., *A Novel Gene Expressed in Rat Ameloblasts Codes for Proteins with Cell binding Domains*, Journal of Bone and Mineral Research, vol. 11, No. 7, pp. 883–891, 1996.
Krebsbach, et al., *Full–Length Sequence, Localization, and Chromosomal Mapping of Ametoblastin*, the Journal of Biological Chemistry, vo. 271, No. 8, pp. 4431–4436, 1996.
Tuszynski, et al., *Biological Activities of Peptides and Peptide Analogues Derived from Common Sequences Present in Thrombospondin, Properdin, and Malarial Protein*, Journal of Cell Biology, vol. 116, pp. 209–217, 1992.
Nasman and Hammerstrom, *Indluence of the antineoplastic agent cyclophosphamide on dental development in rat molars*, Acta Odontol Scand, vol. 64, pp. 287–294, 1996.
Brandsten, et al., *Coronal Dentinal Nodulas Induced by Single or Multiple Injections of HEBP in Young Rats*, Connective Tissue Research, vol. 32, pp. 275–279, 1994.
Yamada and Kleinman, *Functional domains of cell adhesion molecules*, Current Opinion in Cell Biology, vol. 4, pp. 813–823, 1992.
Staatz, et al., *Identification of a Tetrapeptide Recognition Sequence for the α,β, Integrin in Collagen*, Journal of Biological Chemistry, vol. 266, No. 12, pp. 7363–7367, 1991.
Hu, et al., *Sheathlin; Clonin, cDNA/Polypeptide Sequences, and Immunolocalization of Porcine Enamel Sheath Proteins*, vol. 76., pp. 648–657,–1997.
MacDougall, et al., *Ameloblastin gene (AMBU) maps withing the critical region for autosomal document amelogenesis imperfects at chromosome 4 or 21*, Genomics, vol. 41, pp. 115–118 (1997) (abstract only).

* cited by examiner

Primary Examiner—Stephanie Zitomer
Assistant Examiner—Dianne Rees
(74) Attorney, Agent, or Firm—Iver P. Cooper

(57) ABSTRACT

The invention relates to novel nucleic acid fragments encoding polypeptides which are capable of mediating contact between enamel and cell surface. The invention also relates to expression vectors containing the nucleic acid fragments according to the invention for production of the protein, organisms containing said expression vector, methods for producing the polypeptide, compositions comprising the polypeptides, antibodies or antibody fragments recognizing the polypeptides, and methods for treating various hard tissue diseases or disorders.

53 Claims, 8 Drawing Sheets

| | | | | | |
|---|---|---|---|---|---|
| amelin1 | GCTTTTCAGC | TTTGACCCCA | TAGCGTACCT | TATTGCTAAA | ACACTTGCTA CCCTTCCACA GCGAAGGTAT TAAGAGCACT AAGCATGTAT TAATAAATAC 1500 |
| amelin2 | GCTTTTCAGC | TTTGACCCCA | TAGCGTACCT | TATTGCTAAA | ACACTTGCTA CCCTTCCACA GCGAAGGTAT TAAGAGCACT AAGCATGTAT TAATAAATAC |

| | | | | | |
|---|---|---|---|---|---|
| amelin1 | AAGTGCCTAG | AAATAGTGTA | GGTCCCTTCT | TGCTTCCATT | CTTATCGAAA TAAAACATAT CAACTGTCTC CGTGACTTAG AAATACTATC GATGATGTCA 1600 |
| amelin2 | AAGTGCCTAG | AAATAGTGTA | GGTCCCTTCT | TGCTTCCATT | CTTATCGAAA TAAAACATAT CAACTGTCTC CGTGACTTAG AAATACTATC GATGATGTCA |

| | | | | | |
|---|---|---|---|---|---|
| amelin1 | GAGCAAGTCT | GAGTGTCAGC | ACTTGGTGAT | CTAGCATGTA | GCATCATAAA ATTCCTCTTA CTACATGACA TTATTATGCC CAGGAAATGT 1700 |
| amelin2 | GAGCAAGTCT | GAGTGTCAGC | ACTTGGTGAT | CTAGCATGTA | GCATCATAAA ATTCCTCTTA CTACATGACA TTATTATGCC CAGGAAATGT |

| | | | | | |
|---|---|---|---|---|---|
| amelin1 | GACACCGCTT | CTTTCTCTAC | GCAAAAGCAC | TTAGTTTCAG | AATTCCAAAG TATTTCATTT AAACCGTATT AAATGGTGAT TGGTGGAGAA TCCTGACTGC 1800 |
| amelin2 | GACACCGCTT | CTTTCTCTAC | GCAAAAGCAC | TTAGTTTCAG | AATTCCAAAG TATTTCATTT AAACCGTATT AAATGGTGAT TGGTGGAGAA TCCTGACTGC |

| | | | | | |
|---|---|---|---|---|---|
| amelin1 | TATTACTGGG | TATCATATAT | TGGATTTAAA | ATTCTTATTT | ATAGAATATT TTATTAAATC TTAAATGTA AGAAAAGCA TACTCAAAAA GGCCTGTTTT AAATAAAGAA 1900 |
| amelin2 | TATTACTGGG | TATCATATAT | TGGATTTAAA | ATTCTTATTT | ATAGAATATT TTATTAAATC TTAAATAGTA AGAAAAGCA TACTCAAAAA GGCCTGTTTT AAATAAAGAA |

| | | | |
|---|---|---|---|
| amelin1 | TTTTTCTCAC | TGAAAATGTC | AGGAATTGTA | TGCTTATTAT TTAATATGTAT TTAAATAGTA AGAAAAGCA TACTCAAAAA AAAAAA 1986 |
| amelin2 | TTTTTCTCAC | TGAAAATGTC | AGGAATTGTA | TGCTTATTAT TTAATATGTAT TTAAATAGTA AGAAAAGCA TACTCAAAAA AAAAAA |

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 1940 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 95..1315

(xi) SEQUENCE DESCRIPTION: SEQ ID NO: 1:

```
GAGAGAGAGA GCCCCAGGAA CAGTCCAGAA AAAAATTAAT CTTCTTTTCT TAGAACTGTT      60

TTGATTGGCA TCATCAGGCC TGGGAGCACA GTGA ATG TCA GCA TCT AAG ATT         112
```

-continued

```
                        Met Ser Ala Ser Lys Ile
                          1               5
CCA CTT TTC AAA ATG AAG GGC CTG CTC CTG TTC CTG TCC CTA GTG AAA      160
Pro Leu Phe Lys Met Lys Gly Leu Leu Leu Phe Leu Ser Leu Val Lys
            10              15                  20

ATG AGC CTC GCC GTG CCG GCA TTT CCT CAA CAA CCT GGG GCT CAA GGC      208
Met Ser Leu Ala Val Pro Ala Phe Pro Gln Gln Pro Gly Ala Gln Gly
            25              30                  35

ATG GCA CCT CCT GGC ATG GCT AGT TTG AGC CTT GAG ACA ATG AGA CAG      256
Met Ala Pro Pro Gly Met Ala Ser Leu Ser Leu Glu Thr Met Arg Gln
        40              45                  50

TTG GGA AGC TTG CAG GGG CTC AAC GCA CTT TCT CAG TAT TCT AGA CTT      304
Leu Gly Ser Leu Gln Gly Leu Asn Ala Leu Ser Gln Tyr Ser Arg Leu
55              60                  65                  70

GGC TTT GGA AAA GCA CTT AAT AGT TTA TGG TTG CAT GGA CTC CTC CCA      352
Gly Phe Gly Lys Ala Leu Asn Ser Leu Trp Leu His Gly Leu Leu Pro
                75              80                  85

CCG CAT AAT TCT TTC CCA TGG ATA GGA CCA AGG GAA CAT GAA ACC CAA      400
Pro His Asn Ser Phe Pro Trp Ile Gly Pro Arg Glu His Glu Thr Gln
            90              95                  100

CAG CCA TCC TTG CAG CCT CAC CAG CCA GGA CTG AAA CCC TTC CTC CAG      448
Gln Pro Ser Leu Gln Pro His Gln Pro Gly Leu Lys Pro Phe Leu Gln
            105             110                 115

CCC ACT GCT GCA ACC GGT GTC CAG GTC ACA CCC CAG AAG CCA GGG CCT      496
Pro Thr Ala Ala Thr Gly Val Gln Val Thr Pro Gln Lys Pro Gly Pro
        120             125                 130

CAT CCT CCA ATG CAC CCT GGA CAG CTG CCC TTG CAG GAA GGA GAG CTG      544
His Pro Pro Met His Pro Gly Gln Leu Pro Leu Gln Glu Gly Glu Leu
135             140                 145                 150

ATA GCA CCA GAT GAG CCA CAG GTG GCG CCA TCA GAG AAC CCA CCA ACA      592
Ile Ala Pro Asp Glu Pro Gln Val Ala Pro Ser Glu Asn Pro Pro Thr
                155                 160                 165

CCC GAG GTA CCA ATA ATG GAT TTT GCC GAT CCA CAA TTC CCA ACA GTG      640
Pro Glu Val Pro Ile Met Asp Phe Ala Asp Pro Gln Phe Pro Thr Val
            170                 175                 180

TTC CAG ATC GCC CAT TCG CTG TCT CGG GGA CCA ATG GCA CAC AAC AAA      688
Phe Gln Ile Ala His Ser Leu Ser Arg Gly Pro Met Ala His Asn Lys
            185                 190                 195

GTA CCC ACT TTT TAC CCA GGA ATG TTT TAC ATG TCT TAT GGA GCA AAC      736
Val Pro Thr Phe Tyr Pro Gly Met Phe Tyr Met Ser Tyr Gly Ala Asn
        200                 205                 210

CAA TTG AAT GCT CCT GGC AGA ATC GGC TTC ATG AGT TCA GAA GAA ATG      784
Gln Leu Asn Ala Pro Gly Arg Ile Gly Phe Met Ser Ser Glu Glu Met
215                 220                 225                 230

CCT GGA GAA AGA GGA AGT CCC ATG GCC TAC GGA ACT CTG TTC CCA GGA      832
Pro Gly Glu Arg Gly Ser Pro Met Ala Tyr Gly Thr Leu Phe Pro Gly
                235                 240                 245

TAT GGA GGC TTC AGG CAA ACC CTT AGG GGA CTG AAT CAG AAT TCA CCC      880
Tyr Gly Gly Phe Arg Gln Thr Leu Arg Gly Leu Asn Gln Asn Ser Pro
            250                 255                 260

AAG GGA GGA GAC TTT ACT GTG GAA GTA GAT TCT CCA GTG TCT GTA ACT      928
Lys Gly Gly Asp Phe Thr Val Glu Val Asp Ser Pro Val Ser Val Thr
            265                 270                 275

AAA GGC CCT GAG AAA GGA GAG GGT CCA GAA GGC TCT CCA CTG CAA GAG      976
Lys Gly Pro Glu Lys Gly Glu Gly Pro Glu Gly Ser Pro Leu Gln Glu
        280                 285                 290

GCC AGC CCA GAC AAG GGC GAA AAC CCG GCT CTC CTT TCA CAG ATT GCC     1024
Ala Ser Pro Asp Lys Gly Glu Asn Pro Ala Leu Leu Ser Gln Ile Ala
295                 300                 305                 310
```

-continued

```
CCC GGG GCC CAT GCA GGA CTT CTT GCT TTC CCC AAT GAC CAC ATC CCC    1072
Pro Gly Ala His Ala Gly Leu Leu Ala Phe Pro Asn Asp His Ile Pro
            315                 320                 325

AAC ATG GCA AGG GGT CCT GCA GGG CAA AGA CTC CTC GGA GTC ACC CCT    1120
Asn Met Ala Arg Gly Pro Ala Gly Gln Arg Leu Leu Gly Val Thr Pro
            330                 335                 340

GCA GCT GCA GAC CCA CTG ATC ACC CCT GAA TTA GCA GAA GTT TAT GAA    1168
Ala Ala Ala Asp Pro Leu Ile Thr Pro Glu Leu Ala Glu Val Tyr Glu
            345                 350                 355

ACC TAT GGT GCT GAT GTT ACC ACA CCC TTG GGG GAT GGA GAA GCA ACC    1216
Thr Tyr Gly Ala Asp Val Thr Thr Pro Leu Gly Asp Gly Glu Ala Thr
            360                 365                 370

ATG GAT ATC ACC ATG TCC CCA GAC ACT CAG CAG CCA CCG ATG CCT GGA    1264
Met Asp Ile Thr Met Ser Pro Asp Thr Gln Gln Pro Pro Met Pro Gly
375                 380                 385                 390

AAC AAA GTG CAC CAG CCC CAG GTG CAC AAT GCA TGG CGT TTC CAA GAG    1312
Asn Lys Val His Gln Pro Gln Val His Asn Ala Trp Arg Phe Gln Glu
            395                 400                 405

CCC TGACAACCTT GACATAGCAG CTACTTCATG TATGCACAAG CTTTTCAGCT         1365
Pro

TTGACCCCAT AGCGTACCTT ATTGCTAAAA CACTTGCTAC CCTTCCACAG CGAAGGTATT  1425

AAGAGCACTA AGCATGTATT AATAAATACA AGTGCCTAGA AATAGTGTAG GTCCCTTCTT  1485

GCTTCCATTC TTATCGAAAT AAAACATATC AACTGTCTCC GTGACTTAGA AATACTATCG  1545

ATGATGTCAG AGCAAGTCTG AGTGTCAGCA CTTGGTGATC TAGCATGTAG CTGTCTTAGG  1605

CATCATAAAA TTCCTCTTAC TACATGACAT TATTATGCCC AGGAAATGTG ACACCGCTTC  1665

TTTCTCTACG CAAAAGCACT TAGTTTCAGA ATTCCAAAGT ATTTCATTTA AACCGTATTA  1725

AATGGTGATT GGTGGAGAAT CCTGACTGCT ATTACTGGGT ATCATATATT GGATTTAAAA  1785

TTCTTATTTA TAGAATATTT TATTTAATCT AGGAAAAGAA AAGGCAATTG GCCTGTTTTA  1845

AATAAAGAAT TTTTCTCACT GAAAATGTCA GGAATTGTAT GCTTATTATT TATATGTATT  1905

TAAATAGTAA AGAAAAGCAT ACTCAAAAAA AAAAA                             1940
```

(2) INFORMATION FOR SEQ ID NO: 2:

(i) SEQUENCE CHARACTERISTICS:
        (A) LENGTH: 407 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ser Ala Ser Lys Ile Pro Leu Phe Lys Met Lys Gly Leu Leu Leu
1               5                   10                  15

Phe Leu Ser Leu Val Lys Met Ser Leu Ala Val Pro Ala Phe Pro Gln
                20                  25                  30

Gln Pro Gly Ala Gln Gly Met Ala Pro Pro Gly Met Ala Ser Leu Ser
            35                  40                  45

Leu Glu Thr Met Arg Gln Leu Gly Ser Leu Gln Gly Leu Asn Ala Leu
        50                  55                  60

Ser Gln Tyr Ser Arg Leu Gly Phe Gly Lys Ala Leu Asn Ser Leu Trp
65                  70                  75                  80

Leu His Gly Leu Leu Pro Pro His Asn Ser Phe Pro Trp Ile Gly Pro
                85                  90                  95

Arg Glu His Glu Thr Gln Gln Pro Ser Leu Gln Pro His Gln Pro Gly
```

```
                    100                 105                 110
Leu Lys Pro Phe Leu Gln Pro Thr Ala Ala Thr Gly Val Gln Val Thr
        115                 120                 125

Pro Gln Lys Pro Gly Pro His Pro Pro Met His Pro Gly Gln Leu Pro
        130                 135                 140

Leu Gln Glu Gly Glu Leu Ile Ala Pro Asp Glu Pro Gln Val Ala Pro
145                 150                 155                 160

Ser Glu Asn Pro Pro Thr Pro Glu Val Pro Ile Met Asp Phe Ala Asp
                165                 170                 175

Pro Gln Phe Pro Thr Val Phe Gln Ile Ala His Ser Leu Ser Arg Gly
                180                 185                 190

Pro Met Ala His Asn Lys Val Pro Thr Phe Tyr Pro Gly Met Phe Tyr
        195                 200                 205

Met Ser Tyr Gly Ala Asn Gln Leu Asn Ala Pro Gly Arg Ile Gly Phe
        210                 215                 220

Met Ser Ser Glu Glu Met Pro Gly Glu Arg Gly Ser Pro Met Ala Tyr
225                 230                 235                 240

Gly Thr Leu Phe Pro Gly Tyr Gly Gly Phe Arg Gln Thr Leu Arg Gly
                245                 250                 255

Leu Asn Gln Asn Ser Pro Lys Gly Gly Asp Phe Thr Val Glu Val Asp
                260                 265                 270

Ser Pro Val Ser Val Thr Lys Gly Pro Glu Lys Gly Glu Gly Pro Glu
        275                 280                 285

Gly Ser Pro Leu Gln Glu Ala Ser Pro Asp Lys Gly Glu Asn Pro Ala
        290                 295                 300

Leu Leu Ser Gln Ile Ala Pro Gly Ala His Ala Gly Leu Leu Ala Phe
305                 310                 315                 320

Pro Asn Asp His Ile Pro Asn Met Ala Arg Gly Pro Ala Gly Gln Arg
                325                 330                 335

Leu Leu Gly Val Thr Pro Ala Ala Asp Pro Leu Ile Thr Pro Glu
                340                 345                 350

Leu Ala Glu Val Tyr Glu Thr Tyr Gly Ala Asp Val Thr Thr Pro Leu
        355                 360                 365

Gly Asp Gly Glu Ala Thr Met Asp Ile Thr Met Ser Pro Asp Thr Gln
370                 375                 380

Gln Pro Pro Met Pro Gly Asn Lys Val His Gln Pro Gln Val His Asn
385                 390                 395                 400

Ala Trp Arg Phe Gln Glu Pro
                405

(2) INFORMATION FOR SEQ ID NO: 3:

(i) SEQUENCE CHARACTERISTICS:
        (A) LENGTH: 1648 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 52..1023

(xi) SEQUENCE DESCRIPTION: SEQ ID NO: 3:

GAGAGAGAGA GCCACCGCAT AATTCTTTCC CATGGATAGG ACCAAGGGAA C ATG AAA    57
                                                        Met Lys
```

```
CCC AAC AGT ATG GAA AAT TCT TTG CCT GTG CAT CCC CCA CCT CTC CCA        105
Pro Asn Ser Met Glu Asn Ser Leu Pro Val His Pro Pro Pro Leu Pro
410                 415                 420                 425

TCA CAG CCA TCC TTG CAG CCT CAC CAG CCA GGA CTG AAA CCC TTC CTC        153
Ser Gln Pro Ser Leu Gln Pro His Gln Pro Gly Leu Lys Pro Phe Leu
                430                 435                 440

CAG CCC ACT GCT GCA ACC GGT GTC CAG GTC ACA CCC CAG AAG CCA GGG        201
Gln Pro Thr Ala Ala Thr Gly Val Gln Val Thr Pro Gln Lys Pro Gly
            445                 450                 455

CCT CAT CCT CCA ATG CAC CCT GGA CAG CTG CCC TTG CAG GAA GGA GAG        249
Pro His Pro Pro Met His Pro Gly Gln Leu Pro Leu Gln Glu Gly Glu
        460                 465                 470

CTG ATA GCA CCA GAT GAG CCA CAG GTG GCG CCA TCA GAG AAC CCA CCA        297
Leu Ile Ala Pro Asp Glu Pro Gln Val Ala Pro Ser Glu Asn Pro Pro
    475                 480                 485

ACA CCC GAG GTA CCA ATA ATG GAT TTT GCC GAT CCA CAA TTC CCA ACA        345
Thr Pro Glu Val Pro Ile Met Asp Phe Ala Asp Pro Gln Phe Pro Thr
490                 495                 500                 505

GTG TTC CAG ATC GCC CAT TCG CTG TCT CGG GGA CCA ATG GCA CAC AAC        393
Val Phe Gln Ile Ala His Ser Leu Ser Arg Gly Pro Met Ala His Asn
                510                 515                 520

AAA GTA CCC ACT TTT TAC CCA GGA ATG TTT TAC ATG TCT TAT GGA GCA        441
Lys Val Pro Thr Phe Tyr Pro Gly Met Phe Tyr Met Ser Tyr Gly Ala
            525                 530                 535

AAC CAA TTG AAT GCT CCT GGC AGA ATC GGC TTC ATG AGT TCA GAA GAA        489
Asn Gln Leu Asn Ala Pro Gly Arg Ile Gly Phe Met Ser Ser Glu Glu
        540                 545                 550

ATG CCT GGA GAA AGA GGA AGT CCC ATG GCC TAC GGA ACT CTG TTC CCA        537
Met Pro Gly Glu Arg Gly Ser Pro Met Ala Tyr Gly Thr Leu Phe Pro
    555                 560                 565

GGA TAT GGA GGC TTC AGG CAA ACC CTT AGG GGA CTG AAT CAG AAT TCA        585
Gly Tyr Gly Gly Phe Arg Gln Thr Leu Arg Gly Leu Asn Gln Asn Ser
570                 575                 580                 585

CCC AAG GGA GGA GAC TTT ACT GTG GAA GTA GAT TCT CCA GTG TCT GTA        633
Pro Lys Gly Gly Asp Phe Thr Val Glu Val Asp Ser Pro Val Ser Val
                590                 595                 600

ACT AAA GGC CCT GAG AAA GGA GAG GGT CCA GAA GGC TCT CCA CTG CAA        681
Thr Lys Gly Pro Glu Lys Gly Glu Gly Pro Glu Gly Ser Pro Leu Gln
            605                 610                 615

GAG GCC AGC CCA GAC AAG GGC GAA AAC CCG GCT CTC CTT TCA CAG ATT        729
Glu Ala Ser Pro Asp Lys Gly Glu Asn Pro Ala Leu Leu Ser Gln Ile
        620                 625                 630

GCC CCC GGG GCC CAT GCA GGA CTT CTT GCT TTC CCC AAT GAC CAC ATC        777
Ala Pro Gly Ala His Ala Gly Leu Leu Ala Phe Pro Asn Asp His Ile
    635                 640                 645

CCC AAC ATG GCA AGG GGT CCT GCA GGG CAA AGA CTC CTC GGA GTC ACC        825
Pro Asn Met Ala Arg Gly Pro Ala Gly Gln Arg Leu Leu Gly Val Thr
650                 655                 660                 665

CCT GCA GCT GCA GAC CCA CTG ATC ACC CCT GAA TTA GCA GAA GTT TAT        873
Pro Ala Ala Ala Asp Pro Leu Ile Thr Pro Glu Leu Ala Glu Val Tyr
                670                 675                 680

GAA ACC TAT GGT GCT GAT GTT ACC ACA CCC TTG GGG GAT GGA GAA GCA        921
Glu Thr Tyr Gly Ala Asp Val Thr Thr Pro Leu Gly Asp Gly Glu Ala
            685                 690                 695

ACC ATG GAT ATC ACC ATG TCC CCA GAC ACT CAG CAG CCA CCG ATG CCT        969
Thr Met Asp Ile Thr Met Ser Pro Asp Thr Gln Gln Pro Pro Met Pro
        700                 705                 710

GGA AAC AAA GTG CAC CAG CCC CAG GTG CAC AAT GCA TGG CGT TTC CAA       1017
Gly Asn Lys Val His Gln Pro Gln Val His Asn Ala Trp Arg Phe Gln
    715                 720                 725
```

-continued

```
GAG CCC TGACAACCTT GACATAGCAG CTACTTCATG TATGCACAAG CTTTTCAGCT    1073
Glu Pro
730

TTGACCCCAT AGCGTACCTT ATTGCTAAAA CACTTGCTAC CCTTCCACAG CGAAGGTATT   1133

AAGAGCACTA AGCATGTATT AATAAATACA AGTGCCTAGA AATAGTGTAG GTCCCTTCTT   1193

GCTTCCATTC TTATCGAAAT AAAACATATC AACTGTCTCC GTGACTTAGA AATACTATCG   1253

ATGATGTCAG AGCAAGTCTG AGTGTCAGCA CTTGGTGATC TAGCATGTAG CTGTCTTAGG   1313

CATCATAAAA TTCCTCTTAC TACATGACAT TATTATGCCC AGGAAATGTG ACACCGCTTC   1373

TTTCTCTACG CAAAAGCACT TAGTTTCAGA ATTCCAAAGT ATTTCATTTA AACCGTATTA   1433

AATGGTGATT GGTGGAGAAT CCTGACTGCT ATTACTGGGT ATCATATATT GGATTTAAAA   1493

TTCTTATTTA TAGAATATTT TATTTAATCT AGGAAAAGAA AAGGCAATTG GCCTGTTTTA   1553

AATAAAGAAT TTTTCTCACT GAAAATGTCA GGAATTGTAT GCTTATTATT TATATGTATT   1613

TAAATAGTAA AGAAAAGCAT ACTCAAAAAA AAAA                              1648
```

(2) INFORMATION FOR SEQ ID NO: 4:

(i) SEQUENCE CHARACTERISTICS:
        (A) LENGTH: 324 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Lys Pro Asn Ser Met Glu Asn Ser Leu Pro Val His Pro Pro
 1               5                  10                  15

Leu Pro Ser Gln Pro Ser Leu Gln Pro His Gln Pro Gly Leu Lys Pro
                20                  25                  30

Phe Leu Gln Pro Thr Ala Ala Thr Gly Val Gln Val Thr Pro Gln Lys
            35                  40                  45

Pro Gly Pro His Pro Pro Met His Pro Gly Gln Leu Pro Leu Gln Glu
        50                  55                  60

Gly Glu Leu Ile Ala Pro Asp Glu Pro Gln Val Ala Pro Ser Glu Asn
 65                  70                  75                  80

Pro Pro Thr Pro Glu Val Pro Ile Met Asp Phe Ala Asp Pro Gln Phe
                85                  90                  95

Pro Thr Val Phe Gln Ile Ala His Ser Leu Ser Arg Gly Pro Met Ala
            100                 105                 110

His Asn Lys Val Pro Thr Phe Tyr Pro Gly Met Phe Tyr Met Ser Tyr
        115                 120                 125

Gly Ala Asn Gln Leu Asn Ala Pro Gly Arg Ile Gly Phe Met Ser Ser
    130                 135                 140

Glu Glu Met Pro Gly Glu Arg Gly Ser Pro Met Ala Tyr Gly Thr Leu
145                 150                 155                 160

Phe Pro Gly Tyr Gly Gly Phe Arg Gln Thr Leu Arg Gly Leu Asn Gln
                165                 170                 175

Asn Ser Pro Lys Gly Gly Asp Phe Thr Val Glu Val Asp Ser Pro Val
            180                 185                 190

Ser Val Thr Lys Gly Pro Glu Lys Gly Glu Gly Pro Glu Gly Ser Pro
        195                 200                 205

Leu Gln Glu Ala Ser Pro Asp Lys Gly Glu Asn Pro Ala Leu Leu Ser
    210                 215                 220
```

```
Gln Ile Ala Pro Gly Ala His Ala Gly Leu Leu Ala Phe Pro Asn Asp
225                 230                 235                 240

His Ile Pro Asn Met Ala Arg Gly Pro Ala Gly Gln Arg Leu Leu Gly
                245                 250                 255

Val Thr Pro Ala Ala Ala Asp Pro Leu Ile Thr Pro Glu Leu Ala Glu
            260                 265                 270

Val Tyr Glu Thr Tyr Gly Ala Asp Val Thr Thr Pro Leu Gly Asp Gly
            275                 280                 285

Glu Ala Thr Met Asp Ile Thr Met Ser Pro Asp Thr Gln Gln Pro Pro
            290                 295                 300

Met Pro Gly Asn Lys Val His Gln Pro Gln Val His Asn Ala Trp Arg
305                 310                 315                 320

Phe Gln Glu Pro
```

(2) INFORMATION FOR SEQ ID NO: 5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
GGTCGTCATC ACCATCACCA TCACTA                                    26
```

(2) INFORMATION FOR SEQ ID NO: 6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

```
CGATTAGTGA TGGTGATGGT GATGACGACC TGCA                           34
```

(2) INFORMATION FOR SEQ ID NO: 7:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO: 7:

```
Val Pro Ala Phe Pro Arg Gln Pro Gly Thr His Gly Val Ala Ser Leu
1               5                   10                  15
```

(2) INFORMATION FOR SEQ ID NO: 8:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

```
CATGTAGGCA ATGCTGTTCT TGCAGTGGTA GGTGATGTTC TGGGAGGC             48
```

(2) INFORMATION FOR SEQ ID NO: 9:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

ATCCACTTCT TCCCGCTTGG TCTTGTCTGT CGCTGGCCAA GCTTC                             45

NUCLEIC ACIDS ENCODING ENAMEL MATRIX RELATED POLYPEPTIDES

This is division of Ser. No. 08/732,749 filed Oct. 18, 1996, now U.S. Pat. No. 6,300,062, which is a continuation of Serial No. 60/005,634 filed Oct. 19, 1995, now abandoned.

The prior application(s) set forth above are hereby incorporated by reference in their entirety.

FIELD OF INVENTION

The present invention relates to novel nucleic acid sequences which code for polypeptides belonging to a group named amelins, which polypeptide sequences comprise tetrapeptide domains implicated in cell surface recognition. Possible applications of the amelin sequence concern the diagnosis of disorders of hard tissue formation, and the production of the amelin protein or fragments thereof, which may then serve as matrix constituents or cell recognition tags in the formation of biomaterials. The invention also relates to expression vectors containing the nucleic acid sequences according to the invention for production of the protein, organisms containing said expression vector, methods for producing the polypeptide, compositions comprising the polypeptides, and methods for treating various hard tissue diseases or disorders.

TECHNICAL BACKGROUND

In bone, dentin and other tissues, collagen type I or similar proteins assemble into a fibrillar matrix, which in some instances serves as a scaffold for the incorporation of mineral crystals. The adjacent cells establish specific contacts to the matrix, which are mediated by interactions between domains in extracellular proteins such as collagen and receptors of the cell surface, for instance integrins. Peptide domains which are involved in these contacts have been identified in several extracellular proteins (Yamada & Kleinman, 1992). In enamel, a structural network which is comparable to the collagen fibres of bone, cartilage and dentin has not been found. Also, no sequence segments have been identified in the enamel matrix proteins, which could mediate its anchoring to cell adhesion molecules. The enamel proteins amelogenin and enamelin do not contain such protein domains. The mineral content of newly deposited enamel is around 15% of the total mass and increases later, under degradation of the proteins, to 95% (Robinson et al., 1988).

Two predominant groups of proteins have been identified in enamel: enameling and amelogenins (Termine et al., 1980). Protein fragments in mature enamel are similar to one of the enameling, tuftelin, which has been located by antibodies in-between the enamel prisms. The cDNA sequence corresponding to tuftelin has been determined, and it has been speculated that this protein might have a function in the mineralization of enamel (Deutsch et al., 1991). The significance of the remaining, so far described, enameling for enamel formation may be disputed, because the main protein species are identical to proteins from the bloodstream (Strawich & Glimcher, 1990). It is still discussed whether amelogenin, the most frequent enamel protein, provides a scaffold for the enamel matrix (Simmer et al., 1994).

Partial sequences of randomly selected cDNA clones from a rat in situ library have previously been compiled (Matsuki et al., 1995), of which some show homology to sequences of the invention. No reading frame was suggested from the partial sequences. It was not stated if polypeptides are encoded by these sequences and no suggestion as to possible function of such polypeptides were given.

Non-amelogenin proteins have been identified in porcine immature enamel (Uchida et al., 1995). A 15 kDa protein had an N-terminal amino acid sequence (Val-Pro-Ala-Phe-Pro-Arg-Gln-Pro-Gly-Thr-His-Gly-Val-Ala-Ser-Leu (SEQ ID NO:7)) with no homology to previously known enamel proteins. It was proposed that the non-amelogenins comprise a new family of enamel proteins but their function was not suggested. The proteins have not been sequenced completely and their genes are not known.

WO89/08441 relates to a composition for use in inducing binding between parts of living mineralized tissue in which the active constituent originates from a precursor to dental enamel, so called enamel matrix. The composition induces binding by facilitating regeneration of mineralized tissue. The active constituent is part of a protein fraction and is characterized by having a molecular weight of up to about 40.000 kDa but no single protein is identified.

SUMMARY OF THE INVENTION

Although proteins of mineralized matrices are often produced in high amounts, their poor solubility prevents a direct analysis. In the tooth enamel, a physiological degradation of matrix proteins occurs in the course of mineral acquisition during the maturation phase and constitutes an additional difficulty for the analysis of the matrix proteins. The present invention is based upon the consideration that since the matrix forming cells synthesize the corresponding proteins in high amounts, they should contain a high copy number of the mRNAs. Accordingly, sequence analysis of the predominant mRNA species of the matrix forming cells may circumvent part of the problems and help to investigate certain protein constituents of the matrix.

These considerations initiated the approach taken which led to the discovery of the new amelin mRNA sequences, the basis for the present invention. Briefly, a genetic library was constructed containing sequences of the mRNA species of developing teeth. Individual sequences were obtained from single bacterial clones and used for in situ hybridization experiments of histological sections through developing teeth. Sequences which were detected in cells forming hard tissue matrix, e.g. ameloblasts, were determined and used to query sequence databases. Most of the thus selected sequences were represented in the databases but two sequences now termed the amelin sequences were not. These two variants of a new mRNA sequence are expressed at high levels in rat ameloblasts during the formation of the enamel matrix. The sequences contain open reading frames for 407 and 324 amino acid residues, respectively. The encoded proteins, which were named amelins, are rich in proline, leucine and glycine residues and contain the peptide domain Asp-Gly-Glu-Ala, an integrin recognition sequence, in combination with other domains interacting with cell surfaces. The sequences coding for the C-terminal 305 amino acid residues, i.e. amino acids 102–407 in SEQ ID NO:2 and amino acids 19–324 in SEQ ID NO:4, the 3' non-translated part and a microsatellite repeat at the non-translated 5' region are identical in both mRNA variants. The remaining 5' regions contain 338 nucleotides unique to the long variant (nucleotides 13–350 in SEQ ID NO:1), 54 common nucleotides and 46 nucleotides present only in the short variant (nucleotides 66–111 in SEQ ID NO:3). Fourteen nucleotides have the potential to code for 5 amino acids of both proteins in different reading frames (nucleotides 391–404 in SEQ ID NO:1 and 52–65 in SEQ ID NO:3). The reading frame of the longer variant includes codons for a typical N-terminal signal peptide. The properties of the amelin mRNA sequences indicate that amelin is a component of the enamel matrix and the only proteins which have so far been implicated in binding interactions between the ameloblast surface and its extracellular matrix.

It is contemplated that the amelin peptides or parts thereof may be synthesized, either chemically or by translation with the help of expression vectors, by using the sequence information described herein. It is further contemplated that these peptides may contribute to the design of medical devices for the repair of teeth or bones. The peptides may also be combined with artificial implant material for the purpose of improving the biocompatibility of the material. Human amelin mRNA or gene sequences may help in the diagnosis of genetically inherited disorders in hard tissue formation.

BRIEF DESCRIPTION OF THE DRAWINGS

FIG. 1: Localization of RNA sequences in growing first molars. Upper jaws from 4 day old rats were dissected, fixed and embedded in paraffin. Distal-mesial sections through the molars were subjected to in situ hybridization, using DIG labelled RNA complementary to mRNA sequences, prepared by in vitro transcription of Bluescript plasmids.

FIGS. 2A–2C: Sequence of amelins 1 and 2. Several overlapping sequences from both variants were determined and aligned. Identical sequences are printed face to face, dots indicate absence of the corresponding sequences from the respective variant. The longest open reading frames are outlined by amino acid names in the one-letter code. The stretch with two coding frames is shaded (nucleotides 390–403). Underlined are complementary sequences (nucleotides 248–272 and 414–430) to the oligos which were used to screen for clones containing the two variants. Boxes indicate consensus sequences for domains interacting with cell surface proteins. The presumptive polyadenylation signal is double underlined (nucleotides 1892–1897).

DETAILED DESCRIPTION

In order to obtain sequence information on extracellular matrix proteins which may be difficult to analyze in a direct way, a cDNA library was constructed in the bacteriophage λ containing the mRNA repertoire of matrix forming cells. The amelin RNA sequences were selected in the following way:

Replica plaque lifts were performed and hybridized to cDNA and to amelogenin and collagen oligos, respectively, as described in Example 4. Plaques exhibiting a relatively strong hybridization signal with cDNA, but no signal with the oligos were analysed further, assuming that they contained sequences which were frequently represented in cDNA but were different from amelogenin and collagen. Twenty-five of these positive phage clones were converted to Bluescript plasmids.

Figure 1A:
FIG. 1a: amelin.
Figure 1B:
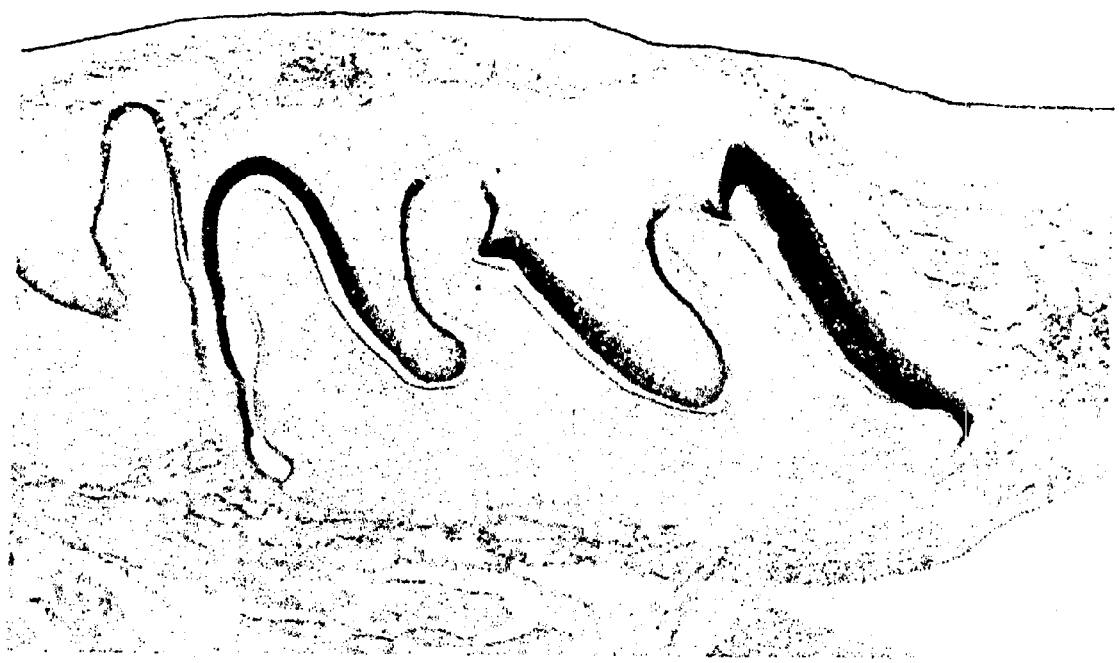
FIG. 1b: amelogenin.
Figure 1C:
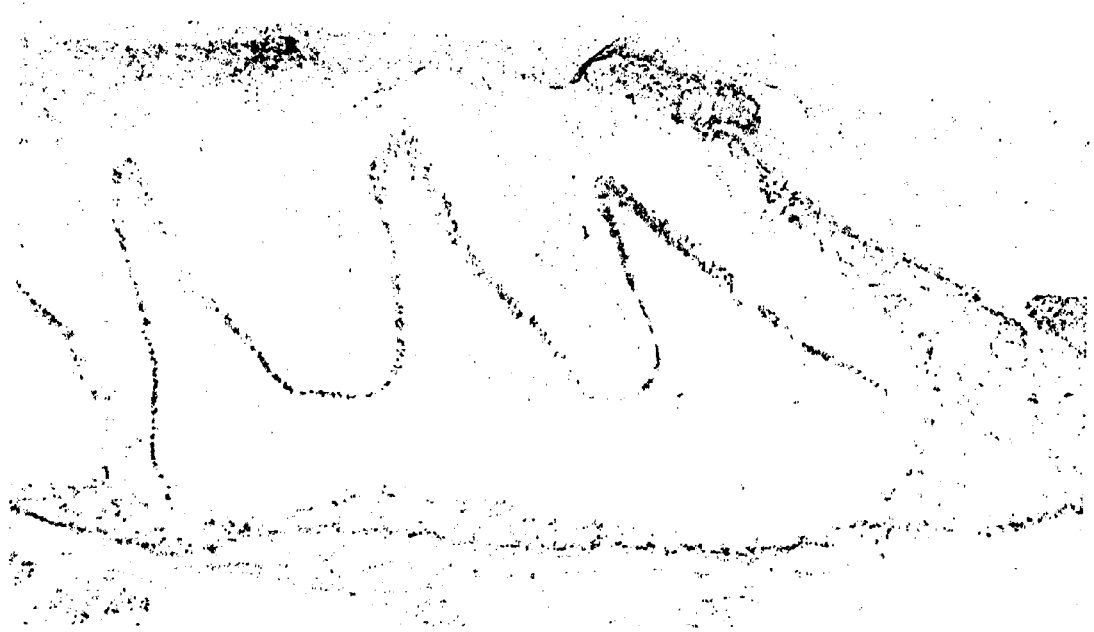
FIG. 1c: collagen type I.

Riboprobes were synthesized for in situ hybridizations, in order to identify the sequences which were expressed in matrix-forming cells, i.e. which may be involved in matrix production and mineralization of growing molars. Rats of 4 days of age were chosen, since the concentration of amelogenin-RNA, implicated in the production of enamel matrix, was highest around this time. FIG. 1 shows the results obtained with an amelin probe (see Example 4 and FIG. 1a), as compared to the reaction of amelogenin RNA (FIG. 1b) and collagen RNA (FIG. 1c). Amelin and amelogenin RNA were detected in the inner enamel epithelium which contains ameloblasts in the secretory phase. The collagen probe decorated mainly the odontoblasts, located peripherally in the mesenchymal pulp, as well as osteoblasts in the alveolar bone. It was therefore concluded that amelin may contribute to the formation of the enamel matrix. Fourteen cDNA inserts which gave rise to probes exhibiting a positive in situ hybridization signal in the tooth structures were partially sequenced. The sequence fragments were used to query the gene bank and EMBL database for their identification. Two hitherto novel sequences were not represented.

Figure 2A:
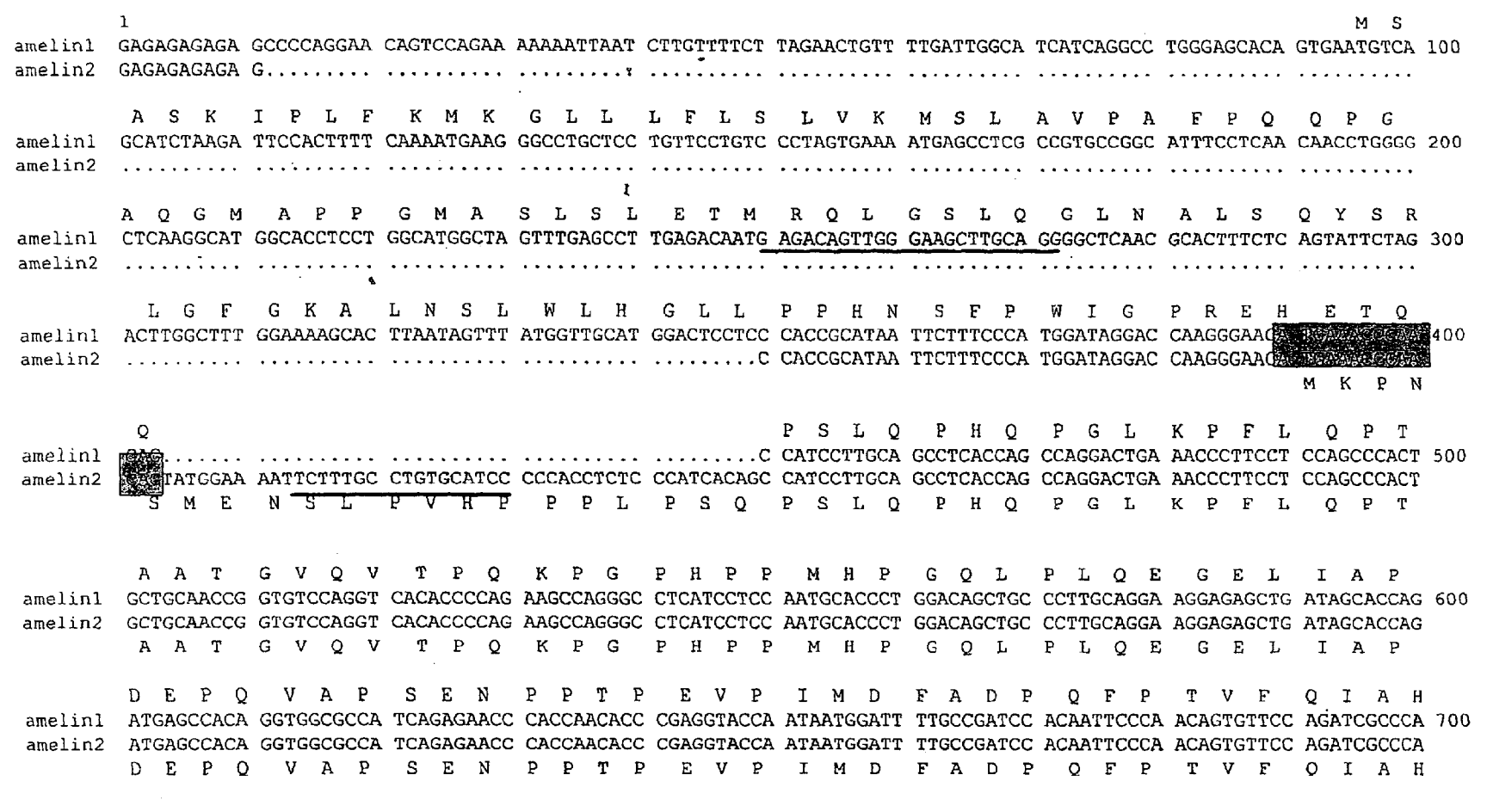
Figure 2B:
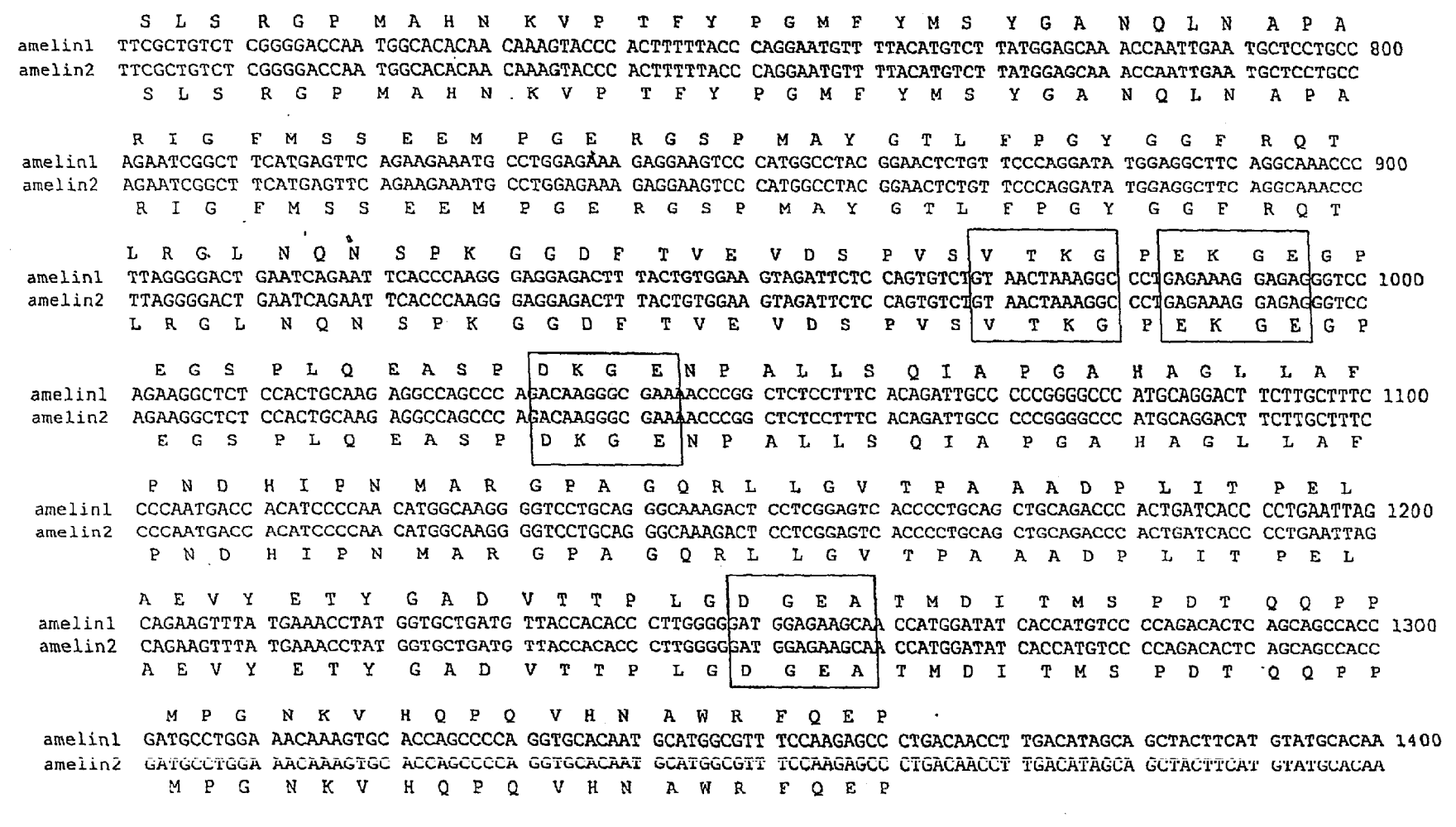

To determine the sequence of the whole amelin mRNA, the tooth cDNA library was screened with an oligonucleotide derived from the initial amelin sequences described above and 6 additional inserts in the range between 0.5 and 2 kb in length were isolated. Sequence analysis showed that all 7 clones represented sequences corresponding to the 3' mRNA portion. However, two different 5' regions were found in the two longest inserts, specifying amelin 1 and amelin 2 (FIG. 2). In order to obtain a full length sequence representation, a random-primed library was constructed from rat molars, and it was screened with two different oligonucleotides, derived from individual 5' ends of the two variants (underlined in FIG. 2). 5 clones were isolated hybridizing with the 5' part of amelin 2 and 13 clones derived from the 5' part of amelin 1. Sequence analysis confirmed the previous results and extended the sequences of both variants, now termed the amelin 1 and amelin 2 sequences and shown in the sequence listing as SEQ ID NO:1 and SEQ ID NO:3, respectively. Both 5' mRNA sequences ended in a polypurine repetition of maximally 100×(AG) (data not shown). Considering the AG repeat at the 5' end and the poly-A tail at the 3' end, the combined sequences (FIG. 2) were not shorter than the mRNAs as determined by Northern blotting (see below). The sequence analysis of the clones obtained from the polyT-primed cDNA library revealed an unexpected 3' variation downstream of the poly-A addition signal AATAAA (double underline). In some clones the poly-A tail was observed 15 nucleotides downstream as expected, but in others at a larger distance of up to 79 nucleotides. The sequence in FIG. 2 shows the most distant polyadenylation site variant. All variations were located downstream of the stop codon.

Both cDNA sequence variants revealed a single long open reading frame (FIG. 2). In-frame termination codons are present between the poly(AG) and the open reading frame, and it therefore does not seem likely that the poly(AG) or proximal sequences code for protein. The reading frame of amelin 1 starts 84 nucleotides downstream of the poly(AG)

repeat. The first 86 amino acids are encoded by a sequence which is not present in amelin 2. The amino acids 87 through 99 of amelin 1 are encoded by a sequence which is common for amelin 1 and amelin 2. However, this sequence cannot code for the amelin 2 protein. Although it includes an ATG codon, an in-frame stop codon would only allow for a heptapeptide. The next ATG, overlapping with the stop codon of the heptapeptide, starts the longest sequence stretch coding for amelin 2. Intriguingly, its first fourteen nucleotides code for both amelin 1 and amelin 2 in different frames (shaded in FIG. 2). The following 46 nucleotides which code for 15 amino acids of amelin 2 are not present in the amelin 1 RNA. This "insert" in amelin 2 RNA results in the synchronization of both reading frames, so that the last 305 amino acid residues are common to both proteins. There is an in-frame ATG codon in the insert of amelin 2, which might serve as an alternative translation start. In this case, amelin 2 would be 5 amino acids shorter and there would be no two frame-coding sequence stretch. The longest possible open reading frame contains codons for 407 amino acid residues for amelin 1 and 324 residues for amelin 2.

Since the filing of the first application the results of the sequencing have been reviewed and some amendments made. The sequence for amelin 1 has been amended as follows: nucleotide no. 133 has been changed from a G to a C resulting in no amino acid change. Nucleotide no. 192 has been changed from a G to an A resulting in a change of Arg33 to Gln33. Nucleotide no 201 has been changed from a G to a C resulting in a change of Gly36 to Ala36. Nucleotide no. 618 has been changed from a G to a C resulting in a change of Gly175 to Ala175. Nucleotide no. 810 has been changed from a G to a C resulting in a change of Gly239 to Ala239. Nucleotide no. 977 has been changed from a C to a G resulting in a change of Pro295 to Ala295. Nucleotide no. 1650 has been changed from a C to an A resulting in no amino acid change. The sequence for amelin 2 has been corrected as follows: nucleotide no. 326 has been changed from a G to a C resulting in a change of Gly92 to Ala92. Nucleotide no. 518 has been changed from a G to a C resulting in a change of G1yl56 to Ala156. Nucleotide no. 685 has been changed from a C to a G resulting in a change of Pro212 to Ala212. Nucleotide no. 1358 has been changed from a C to an A resulting in no amino acid change.

Figure 3:
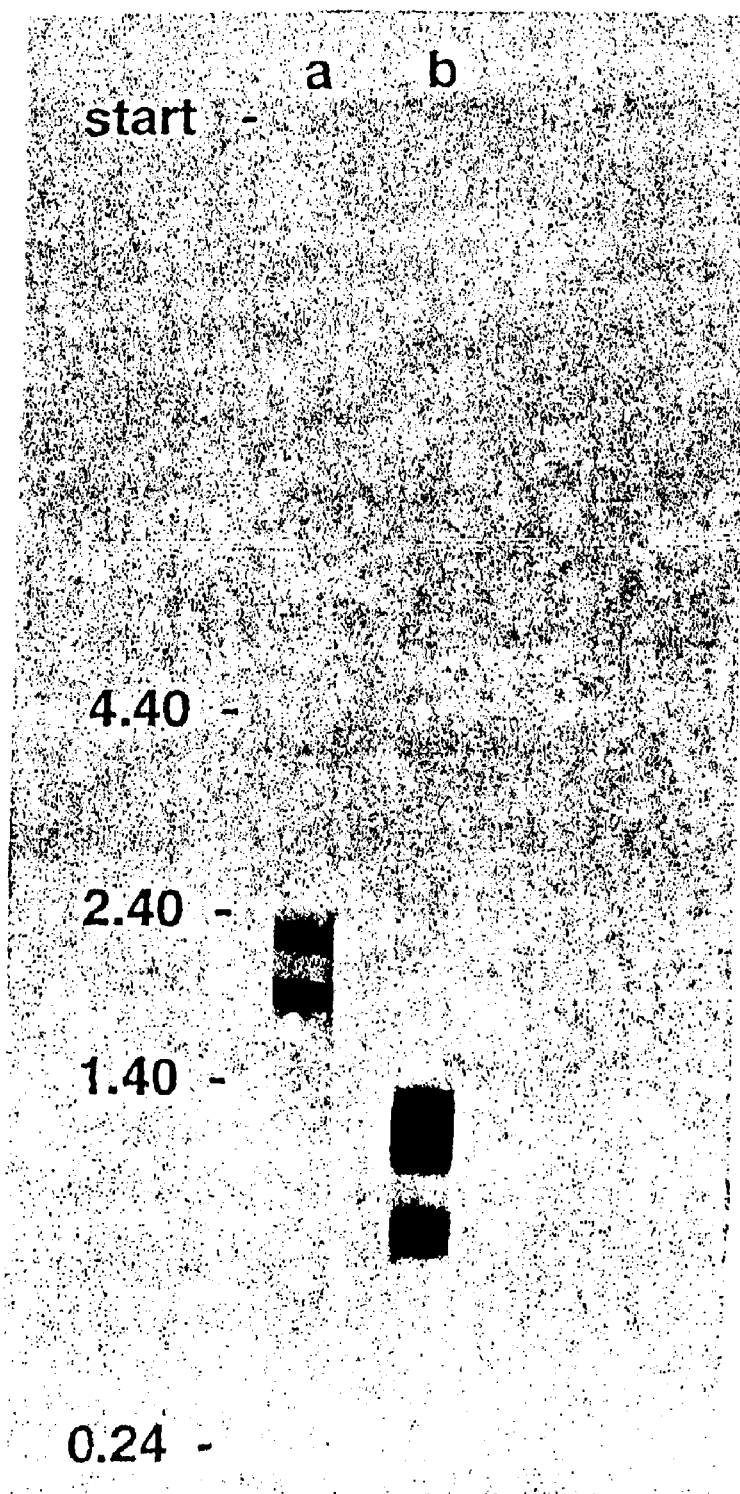
FIG. 3: Northern blot analysis of RNA from rat molars. First molars were dissected from four day old rats. RNA was isolated, four mg per lane were electrophoresed in an agarseformaldehyde gel and transferred to a nylon membrane. Individual lanes were hybridized to amelin (a) the amelogenin (b) DIG-labelled riboprobes. The positions of defined RNA fragments (Gibco BRL) with their length in kb are indicated at the left margin.
Figure 4:
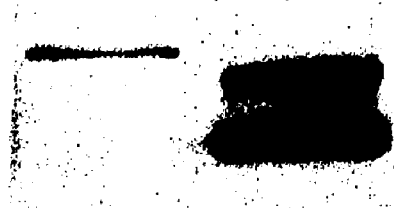
FIG. 4: Immunoblot analysis of (A) recombinant thioredoxin-amelin fusion protein eluted from Ni column, and (B) pH 10.8 extract of rat molars. The samples were separated by one-dimensional SDS-PAGE, transferred to a nitrocellulose membrane and incubated with affinity-purified thioredoxin-amelin antibody. The antigen-antibody complex was identified by secondary goat anti-rabbit-IgG antibody carrying horseradish peroxidase.

To assess the size of amelin transcripts, Northern blot analysis was carried out on total RNA prepared from molars of 4 day old rats (FIG. 3, lane a). The DIG labelled amelin cRNA probe hybridized to a 2.2 kb as well as to a 1.9 kb RNA band. The amelin 1 and amelin 2 mRNAs as determined by cDNA sequence analysis are 2.3 and 2.0 kb long, if a poly(AG) repeat of 0.2 kb and a poly-A tail of 0.2 kb are added to the displayed sequences. The two determinations correspond well, suggesting that the sequences comprise all or almost all of the mRNA for amelins. For a comparison, the two predominant mRNAs for amelogenin, 1.1 kb and 0.8 kb in length, are shown (FIG. 3, lane b). The mass proportion of amelin RNA relative to amelogenin RNA in total RNA from molars was determined by a solution hybridization assay (Mathews et al., 1989). The amount of amelin RNA was about 5% if compared to the content of amelogenin RNA. The sequence comparison of amelin 1 and 2 suggests that the two RNAs are splicing variants of the same primary transcript, since no change in the aligning sequence parts is found.

The most frequent amino acids in both amelin 1 and 2 are proline, glycine and leucine; there is no cysteine in either sequence (vide table 1 below). The amino terminus of the deduced amelin 1 protein has the characteristic feature of a signal peptide: residues 14 to 21 are hydrophobic with a stretch of leucines (FIG. 2; Leader, 1979). No comparable motive is observed in the amelin 2 sequence. Both amelins contain the peptide domain DGEA (Asp-Gly-Glu-Ala) (amino acids 370–373 in amelin 1 and 287–290 in amelin 2) (boxed in FIG. 2), which has earlier been identified to constitute a recognition site of collagen type I for the cell surface protein a2b1 integrin (Staatz et al., 1991). In addition, a thrombospondin-like cell adhesion domain with the sequence VTKG (Val-Thr-Lys-Gly) (amino acids 277–280 in amelin 1 and 194–197 in amelin 2) (Yamada & Kleinman, 1992) is included.

The presence of these two domains indicates that amelins are components of the extracellular matrix. The predicted low solubility of the amelins in water solutions is consistent with this model. The presence of a signal sequence in amelin 1 corroborates the interpretation as a secretory protein. The lack of a signal sequence in amelin 2 does not mean that this protein is not secreted. A precedence for a secreted protein without signal sequence is the chicken ovalbumin, where internal, non-cleaved sequences provide the same function (discussed in Leader, 1979). Two further domains with predicted significance in the interaction with cell surfaces, EKGE (Glu-Lys-Gly-Glu) (amino acids 282–285 in amelin 1 and 199–202 in amelin 2) and DKGE (Asp-Lys-Gly-Glu) (amino acids 298–301 in amelin 1 and 215–218 in amelin 2), are clustered in the same region. The combination of the four peptide domains as described in this paragraph is a feature which has so far not been described for any enamel matrix related protein.

Because of predicted low solubility, amelin was expressed in E. coli cells as a fusion protein with thioredoxin in the amino-terminal end. 6His tag was added to the carboxy terminal end and protein was purified on Ni column. The eluate contained one main fusion protein and also several peptide fragments which were active with antiamelin rabbit serum in Western blot analysis. The protein could be further purified by antithioredoxin affinity chromatography.

Antibodies have been raised against the amelin protein. Rabbits were immunized with amelin-thioredoxin fusion protein and immune serum purified by affinity chromatography on amelin fusion protein coupled to CNBr-activated SEPHAROSE agarose. Further purification might be achieved on thioredoxin-coupled SEPHAROSE agarose. These antibodies have been used for, e.g. immunohistochemical localization of amelin in rat teeth.

Also, the presence of amelin in tooth extract has been established. Rat molars were homogenized in Na-carbonate buffer pH 10.8, 1 mM EDTA+ protease inhibitors. Supernatant of crude extract was analyzed by Western blotting with anti-amelinthioredoxin immune serum. Crude extract was further chromatographed on Sephadex G100 column. Fractions corresponding to molecular weights of amelins were concentrated and subjected to preparative electrophoresis. After electroelution, the bands are now identified by N-terminal sequence analysis. In case one of the bands is amelin, in vivo transformation start is determined.

The expression of the amelin sequence during different developing stages of the tooth has been examined by investigating the upper jaws of Sprague-Dawley rats of 2, 5, 10, 15, 20 and 25 days of age. It was found that amelin mRNA appears in in situ hybridization experiments concomitantly with amelogenin mRNA, i.e. during the elongation of the ameloblasts at the beginning of the secretory stage. In later stages, amelogenin and amelin mRNA exhibit profoundly different hybridization patterns. Amelogenin mRNA disappears to a great extent in the maturation stage with only small amounts remaining at a later stage of matured ameloblasts, this observation being in agreement with the findings of Wurtz et al. (1995). The signal obtained with the amelin probe, however, was not or only to a little extent reduced during the maturation stage of the ameloblasts.

Functionally, the two stages are different in that no additional enamel matrix is deposited during the maturation phase. However, mineral seems to be deposited in both phases, since the newly deposited enamel already contains mineral. In correlating these events with the appearance of the respective mRNAs, it is possible that amelin is involved in the mineralization process. The amelin mRNA sequence codes as described above for a protein which contains cell binding domains, suggesting that it is also or alternatively involved in the binding of the ameloblasts to the enamel surface.

Amelin protein may function as a proteinase. This has been tested by cutting off and electroeluting the main fusion protein band from the acrylamide gel. After overnight incubation at room temperature, the fusion protein appeared as 3 bands. The control incubation at 4° C. gave only one band. This suggested that degradation takes place at the higher temperature. Further experiments are required to determine whether amelin in fact functions a proteinase.

The present invention provides nucleic acid sequences which code for proteins with a specific combination of cell binding domains. The proteins are components of hard tissue matrices and mediate the contact to the cell surface. The protein coding sequence is presented in FIG. 2 and stretches from nucleotide positions 95 to 1361. The new combination of cell binding domains occupies nucleotide positions 969 to 1259. The individual binding domains may be combined in the present form or displayed in the context of different amino acid surroundings or incorporated into polymers of non-protein nature. Both the nucleic acid sequence and the derived peptide sequences may be used, firstly, as tools for the artificial expression of amelin protein according to standard techniques (Ausubel et al., 1994), secondly, as information for the chemical synthesis of peptides. The sequences may be used to establish diagnostic criteria for the identification of disorders in hard tissue formation, and as means for the production of biomaterials in tissue engineering. In addition, the invention provides expression vectors which contain the claimed sequences positioned downstream of a transcriptional promoter, as well as procedures for the production and isolation of amelin which are based on the use of said expression vectors.

The present invention relates to all enamel matrix related polypeptides which contain at least one sequence element which can mediate the anchoring of the polypeptide to cell adhesion molecules.

By the term "enamel matrix related polypeptide" is, in its broadest aspect, meant a polypeptide which is an enamel matrix protein or a synthetically produced protein with similar properties i.e. which is capable of mediating contact between enamel and cell surface as described in further detail in the following.

In the present specification and claims, the term "polypeptide" comprises both short peptides with a length of at least two amino acid residues and at most 10 amino acid residues and oligopeptides (11–100 amino acid residues) as well as proteins (the functional entity comprising at least one peptide, oligopeptide, or polypeptide which may be chemically modified by being glycosylated, by being lipidated, or by comprising prosthetic groups). The definition of polypeptides also comprises native forms of peptides/proteins in animals including humans as well as recombinant proteins or peptides in any type of expression vectors transforming any kind of host, and also chemically synthesized peptides.

The polypeptides of the invention which have been termed amelin proteins are different from the known enamel matrix proteins amelogenin and enamelin in that they contain at least one sequence element which can mediate the anchoring of the polypeptide to cell adhesion molecules. In particular, they contain a sequence element selected from the group consisting of the tetrapeptides DGEA (Asp-Gly-Glu-Ala), VTKG (Val-Thr-Lys-Gly), EKGE (Glu-Lys-Gly-Glu) and DKGE (Asp-Lys-Gly-Glu).

Preferred embodiments of the present invention are polypeptides having the amino acid sequence SEQ ID NO:2 or an analogue or variant thereof as well as polypeptides having the amino acid sequence SEQ ID NO:4 or an analogue or variant thereof, and polypeptides having a subsequence of the amino acid sequences SEQ ID NO:2 or SEQ ID NO:4.

In a further aspect, the invention relates to nucleic acid fragments encoding polypeptides which are capable of mediating contact between enamel and cell surface. By the term "nucleic acid" is meant a polynucleotide of high molecular weight which can occur as either DNA or RNA and may be either single-stranded or double-stranded.

Although nucleic acid fragments which encode a polypeptide comprising amino acid residues 1 to 407 of SEQ ID NO:2 and nucleic acid fragments which encode a polypeptide comprising amino acid residues 1 to 302 of SEQ ID NO:4 are preferred embodiments, the invention also relates to a nucleic acid fragment encoding a polypeptide having the amino acid sequence shown in SEQ ID NO:2 or an analogue or a variant thereof and to a nucleic acid fragment encoding a polypeptide having the amino acid sequence shown in SEQ ID NO:4 or an analogue or a variant thereof.

By the term "a polypeptide having the amino acid sequence shown in SEQ ID NO:2 (or SEQ ID NO:4) or an analogue or a variant thereof" is meant a polypeptide which has the amino acid sequence SEQ ID NO:2 (or SEQ ID NO:4) as well as polypeptides having analogues or variants of said sequence which are produced when a nucleic acid fragment of the invention is expressed in a suitable expression system and which are capable of mediating contact between enamel and cell surface, evidenced by a test system comprising extracellular matrix and matrix forming cells in tissue culture. A concentration dependent biological activity of the polypeptides is tested by the addition of polypeptide fragments. If the fragments are capable of competing out contact between the extracellular matrix protein and the cells, then the cells will be detached from the matrix evidenced by microscopic inspection. Cultured cells are known to adhere to fibronectin, osteopontin, collagen, laminin and vitronectin. Cell binding activity is mediated through the RGD cell attachment domain of the protein. Amelin contains alternative cell binding domains DGEA and VTKG. Cell attachment can be measured, e.g., by coating cell culture dishes amelin, BSA or fibronectin. Bound UMR rat osteosarcoma cells can be quantitated by measuring endogenous N-acetyl-β-D-hexosaminidase.

The analogue or variant will thus be a polypeptide which does not have exactly the amino acid sequence shown in SEQ ID NO:2 or in SEQ ID NO:4, but which still is capable of mediating contact between enamel and cell surface as defined above. Generally, such polypeptides will be polypeptides which vary e.g. to a certain extent in the amino acid composition, or the post-translational modifications e.g. glycosylation or phosphorylation, as compared to the amelin proteins described in the examples.

The term "analogue" or "variant" is thus used in the present context to indicate a protein or polypeptide of a similar amino acid composition or sequence as the characteristic amino acid sequences SEQ ID NO:2 and SEQ ID NO:4 derived from the amelin proteins as described in the examples, allowing for minor variations that alter the amino acid sequence, e.g. deletions, exchange or insertions of amino acids, or combinations thereof, to generate amelin protein analogues. These modifications may give interesting and useful novel properties of the analogue. The analogous polypeptide or protein may be derived from an animal or a human or may be partially or completely of synthetic origin. The analogue may also be derived through the use of recombinant DNA techniques.

An important embodiment of the present invention thus relates to a polypeptide in which at least one amino acid residue has been substituted with a different amino acid residue and/or in which at least one amino acid residue has been deleted or added so as to result in a polypeptide comprising an amino acid sequence being different from the amino acid sequence shown in SEQ ID NO:2 or SEQ ID NO:4 or a subsequence of said amino acid sequence as defined in the following, but essentially having amelin activity as defined above.

An interesting embodiment of the invention relates to a polypeptide which is an analogue or subsequence of the polypeptide of the invention comprising from 6 to 300 amino acids, e.g. at least 10 amino acids, at least 30 amino acids, such as at least 60, 90 or 120 amino acids, at least 150 amino acids or at least 200 amino acids.

Particularly important embodiments of the invention are the polypeptide containing the amino acid residues 1–407 in SEQ ID NO:2 (amelin 1) and the polypeptide containing the amino acid residues 1–324 in SEQ ID NO:4 (amelin 2).

The amino acid sequences SEQ ID NO:2 and SEQ ID NO:4 have been compared with known amino acid sequences. The degree of homology (or identity) with the extracellular matrix proteins with which the homology is highest, amelogenin and collagen TV, is very low. The identity is spread over the entire protein and not restricted to particular areas. In this respect it should be noted that amelin does not contain a repeated triple motif in contrast to collagen which is always encoded by the repeated triple motif, Gly-X-Y. The homology to collagen IV and amelogenin may be due to the high content of proline in both proteins. It thus appears that the amelin proteins only have moderate similarity with previously known extracellular proteins, in particular enamel matrix proteins.

An important embodiment of the present invention relates to a polypeptide having an amino acid sequence from which a consecutive string of 20 amino acids is homologous to a degree of at least 80% with a string of amino acids of the same length selected from the amino acid sequence shown in SEQ ID NO:2 or SEQ ID NO:4.

Polypeptide sequences of the invention which have a homology or identity of at least 80% such as at least 85%, e.g. 90%, with the polypeptide shown in SEQ ID NO:2 or SEQ ID NO:4 constitute important embodiments. As the sequences shown in SEQ ID NO:2 and SEQ ID NO:4 seem to be quite unique, the scope of the invention also comprises polypeptides for which the degree of homology to a similar consecutive string of 20 amino acids selected from the amino acid sequence shown in SEQ ID NO:2 or SEQ ID NO:4 is at least 25%, such as at least 50% or at least 75%. Such sequences may be derived from similar proteins from other species, e.g. other mammals such as mouse, rabbit, guinea pig, pig, cow or human.

By use of the sequences disclosed in the present application, the person skilled in the art will be able to detect, clone, sequence, produce, and study the human version of amelin. A practical problem is a scarcity of the starting material, as the most convenient tooth material available is the extracted or resected teeth, mainly the third molars or the supernumerary teeth. The stage of development of these teeth is usually quite late and therefore, the cells involved in the matrix formation are far behind the secretory phase or are not present any more.

Alternatively, the starting material can be derived from available tissue cultures where the extracted RNA is tested for the presence of amelin messengers. Positive Northern blot was obtained in case of human osteosarcoma cells (Saos 2 cells), although the detected length of positive RNA is considerably smaller compared to rat amelin mRNAs.

Thus, a human osteosarcoma cells (Saos 2 cells) cDNA library is constructed in order to find one or more specific cDNAs that would represent human versions of amelin or amelin-like structures. In a similar manner, cDNA libraries from the least developed teeth can be created and screened with rat amelin probes or with probes obtained from the Saos 2 library.

By the term "sequence homology" is meant the identity in sequence of amino acids in segments of two or more amino acids in the match with respect to identity and position of the amino acids of the polypeptides.

The term "homologous" is thus used here to illustrate the degree of identity between the amino acid sequence of a given polypeptide and the amino acid sequence shown in SEQ ID NO:2 or SEQ ID NO:4. The amino acid sequence to be compared with the amino acid sequence shown in SEQ ID NO:2 or SEQ ID NO:4 may be deduced from a nucleotide sequence such as a DNA or RNA sequence, e.g. obtained by hybridization as defined in the following, or may be obtained by conventional amino acid sequencing methods. The degree of homology is preferably determined on the amino acid sequence of a mature polypeptide, i.e. without taking any leader sequence into consideration. Generally, only coding regions are used when comparing nucleotide sequences in order to determine their internal homology.

In one of its aspects, the invention relates to a nucleic acid fragment encoding a polypeptide of the invention as defined above. In particular, the invention relates to a nucleic acid fragment comprising substantially the sequence shown in SEQ ID NO:1 or comprising substantially the sequence shown in SEQ ID NO:3.

The present invention also relates to nucleic acid fragments which hybridize with a nucleic acid fragment having the nucleotide sequence shown in SEQ ID NO:1 or the nucleotide sequence shown in SEQ ID NO:3 or parts of said sequences which are stable under stringent conditions e.g. 5 mM monovalent ions (0.1×SSC), neutral pH and 65° C.

In another aspect, the invention relates to analogues or subsequences of the nucleotide sequence shown in SEQ ID NO:1 or the nucleotide sequence shown in SEQ ID NO:3 of at least 18 nucleotides which
  1) have a homology with the sequence shown in SEQ ID NO:1 or SEQ ID NO:3 of at least 90%, and/or
  2) encode a polypeptide, the amino acid sequence of which is at least 80% homologous with the amino acid sequence shown in SEQ ID NO:2 or SEQ ID NO:4.

The present invention also relates to a nucleic acid fragment encoding a polypeptide having a subsequence of the amino acid sequences SEQ ID NO:2 or SEQ ID NO:4. In the present specification and claims, the term "subsequence" designates a sequence which preferably has a size of at least 15 nucleotides, more preferably at least 18 nucleotides, and most preferably at least 21 nucleotides. In a number of embodiments of the invention, the subsequence or analogue of the nucleic acid fragment of the invention will comprise at least 48 nucleotides, such as at least 75 nucleotides or at least 99 nucleotides. The "subsequence" should conform to at least one of the criteria 1) and 2) above or should hybridize with a nucleic acid fragment comprising the nucleotide sequence shown in SEQ ID NO:1 or the nucleotide sequence shown in SEQ ID NO:3.

It is well known that small fragments are useful in PCR techniques as is described herein. Such fragments and subsequences may among other utilities be used as probes in the identification of mRNA fragments of the nucleotide sequence of the invention as described in Example 4.

The term "analogue" with regard to the nucleic acid fragments of the invention is intended to indicate a nucleic acid fragment which encodes a polypeptide which is functionally similar to the polypeptide encoded by SEQ ID NO:2 and SEQ ID NO:4 in that the analogue is capable of mediating the anchoring of the polypeptide to cell adhesion molecule as evidenced by the test described above.

It is well known that the same amino acid may be encoded by various codons, the codon usage being related, inter alia, to the preference of the organisms in question expressing the nucleotide sequence. Thus, one or more nucleotides or codons of the nucleic acid fragment of the invention may be exchanged by others which, when expressed, result in a polypeptide identical or substantially identical to the polypeptide encoded by the nucleic acid fragment in question.

Also, the term "analogue" is used in the present context to indicate a nucleic acid fragment encoding an amino acid sequence constituting an amelin-like polypeptide, allowing for minor variations in the nucleotide sequences which do not have a significant adverse effect on the capability of mediating contact between enamel and cell surface evidenced by the test described above.

By the term "significant adverse effect" is meant that the activity of the analogue should be at least 10%, more preferably at least 20%, even more preferably at least 25% such as at least 50% of the attachment or detachment activity of native amelin, when determined as described above. The analogous nucleic acid fragment or nucleotide sequence may be derived from an organism such as an animal or a human or may be partially or completely of synthetic origin. The analogue may also be derived through the use of recombinant DNA techniques.

Furthermore, the terms "analogue" and "subsequence" are intended to allow for variations in the sequence such as substitution, insertion (including introns), addition and rearrangement of one or more nucleotides, which variations do not have any substantial adverse effect on the polypeptide encoded by the nucleic acid fragment or a subsequence thereof.

The term "substitution" is intended to mean the replacement of one or more nucleotides in the full nucleotide sequence with one or more different nucleotides, "addition" is understood to mean the addition of one or more nucleotides at either end of the full nucleotide sequence, "insertion" is intended to mean the introduction of one or more nucleotides within the full nucleotide sequence, "deletion" is intended to indicate that one or more nucleotides have been deleted from the full nucleotide sequence whether at either end of the sequence or at any suitable point within it, and "rearrangement" is intended to mean that two or more nucleotide residues have been exchanged within the nucleic acid or polypeptide sequence, respectively. The nucleic acid fragment may, however, also be modified by mutagenesis either before or after inserting it into the organism.

The terms "fragment", "sequence", "subsequence" and "analogue", as used in the present specification and claims with respect to fragments, sequences, subsequences and analogues according to the invention, should of course be understood as not comprising these phenomena in their natural environment, but rather, e.g., in isolated, purified, in vitro or recombinant form.

In one embodiment of the invention, detection of genetic mutations and/or quantitation of amelin mRNA may be obtained by extracting RNA from cells or tissues and converting it into cDNA for subsequent use in the polymerase chain reaction (PCR). The PCR primer(s) may be synthesized based on a nucleic acid fragment of the invention such as the nucleic acid fragment shown in SEQ ID NO:1 or SEQ ID NO:3. This method for detection and/or quantitation may be used as a diagnostic method for diagnosing a disease condition in which an amelin mRNA is expressed in higher or lower amounts than normally.

Also within the scope of the present invention is a diagnostic agent comprising a nucleotide probe which is capable of detecting a nucleic acid fragment of the invention as well as a method for diagnosing diseases in which the expression of amelin is deregulated and/or diseases where the amelin gene is mutated, comprising subjecting a sample from a patient suspected of having a disease where a higher amount of amelin protein than normally is present or a mutated form of amelin, to a PCR analysis in which the sample is contacted with a diagnostic agent as described above, allowing any nucleic acid fragment to be amplified and determining the presence of any identical or homologous nucleic acid fragments in the sample. In a further aspect, the invention also relates to a diagnostic agent which comprises an amelin polypeptide according to the invention.

The polypeptides of the invention can be produced using recombinant DNA technology. An important embodiment of the present invention relates to an expression system comprising a nucleic acid fragment of the invention. In particular, the invention relates to a replicable expression vector which carries and is capable of mediating the expression of a nucleic acid fragment according to the invention.

Within the scope of the present invention is an organism which carries an expression system according to the invention. Organisms which may be used in this aspect of the invention comprise a microorganism such as a bacterium of the genus Bacillus, Escherichia or Salmonella, a yeast such as Saccharomyces, Pichia, a protozoan, or cell derived from a multicellular organism such as a fungus, an insect cell, a plant cell, a mammalian cell or a cell line. If the organism is a bacterium, it is preferred that the bacterium is of the genus Escherichia, e.g. E. coli. Irrespective of the type of organism used, the nucleic acid fragment of the invention is introduced into the organism either directly or by means of a suitable vector. Alternatively, the polypeptides may be produced in the mammalian cell lines by introducing the nucleic acid fragment or an analogue or a subsequence thereof of the invention either directly or by means of an expression vector.

The nucleic acid fragment or an analogue or a subsequence thereof can also be cloned in a suitable stable expression vector and then put into a suitable cell line. The cells producing the desired polypeptides are then selected based on levels of productivity under conditions suitable for the vector and the cell line used. The selected cells are grown further and form a very important and continuous source of the desired polypeptides. The organism which is used for the production of the polypeptide of the invention may also be a higher organism, e.g. an animal.

An example of a specific analogue of the nucleic acid sequence of the invention is a DNA sequence which comprises the DNA sequence shown in SEQ ID NO:1 or SEQ ID NO:3 or a part thereof and which is particularly adapted for expression in *E. coli*. This DNA sequence is one which, when inserted in *E. coli* together with suitable regulatory sequences, results in the expression of a polypeptide having substantially the amino acid sequence shown in SEQ ID NO:2 or SEQ ID NO:4 or a part thereof. Thus, this DNA sequence comprises specific codons recognized by *E. coli*.

In the present context, the term "gene" is used to indicate a nucleic acid sequence which is involved in producing a polypeptide chain and which includes regions preceding and following the coding region (5'-upstream and 3'-downstream sequences) as well as intervening sequences, introns, which are placed between individual coding segments, exons, or in the 5'-upstream or 3'-downstream region. The 5'-upstream region comprises a regulatory sequence which controls the expression of the gene, typically a promoter. The 3'-downstream region comprises sequences which are involved in termination of transcription of the gene and optionally sequences responsible for polyadenylation of the transcript and the 3'-untranslated region. The present invention also relates to an expression system comprising a nucleic acid fragment as described above encoding a polypeptide of the invention, the system comprising a 5'-flanking sequence capable of mediating expression of said nucleic acid fragment.

The invention furthermore relates to a plasmid vector containing a nucleic acid sequence coding for a polypeptide of the invention or a fusion polypeptide as defined herein. In one particular important embodiment, the nucleic acid fragment or an analogue or subsequence thereof of the invention or a fusion nucleic acid fragment of the invention as defined herein may be carried by a replicable expression vector which is capable of replicating in a host organism or a cell line.

The vector may in particular be a plasmid, phage, cosmid, mini-chromosome or virus. In an interesting embodiment of the invention, the vector may be a vector which, when introduced in a host cell, is integrated in the host cell genome.

In one particular aspect of the invention, the nucleic acid fragment of the invention may comprise another nucleic acid fragment encoding a polypeptide different from or identical to the polypeptide of the invention fused in frame to a nucleic acid fragment of the sequence shown in SEQ ID NO:1 or SEQ ID NO:3 or analogues thereof encoding an amelin polypeptide with the purpose of producing a fused polypeptide. When using recombinant DNA technology the fused nucleic acid sequences may be inserted into a suitable vector or genome. Alternatively, one of the nucleic acid fragments is inserted into the vector or genome already containing the other nucleic acid fragment. A fusion polypeptide can also be made by inserting the two nucleic acid fragments separately and allowing the expression to occur. The host organism, which may be of eukaryotic or prokaryotic origin, is grown under conditions ensuring expression of fused sequences. The fused polypeptide is then purified and the polypeptide of the invention separated from its fusion partner using a suitable method.

One aspect of the invention thus relates to a method of producing a polypeptide of the invention, comprising the following steps of:

(a) inserting a nucleic acid fragment of the invention into an expression vector, (b) transforming a suitable host organism with the vector produced in step (a), (c) culturing the host organism produced in step (b) under suitable conditions for expressing the polypeptide, (d) harvesting the polypeptide, and (e) optionally subjecting the polypeptide to post-translational modification.

Within the scope of the present invention is also a method as described above wherein the polypeptide produced is isolated by a method comprising one or more steps like affinity chromatography using immobilized amelin polypeptide or antibodies reactive with said polypeptide and/or other chromatographic and electrophoretic procedures.

The polypeptide produced as described above may be subjected to post-translational modifications as a result of thermal treatment, chemical treatment (formaldehyde, glutaraldehyde etc.) or enzyme treatment (peptidases, proteinases and protein modification enzymes). The polypeptide may be processed in a different way when produced in an organism as compared to its natural production environment. As an example, glycosylation is often achieved when the polypeptide is expressed by a cell of a higher organism such as yeast or preferably a mammal. Glycosylation is normally found in connection with amino acid residues Asn, Ser, Thr or hydroxylysine. It may or may not be advantageous to remove or alter the processing characteristics caused by the host organism in question.

Subsequent to the expression according to the invention of the polypeptide in an organism or a cell line, the polypeptide can either be used as such or it can first be purified from the organism or cell line. If the polypeptide is expressed as a secreted product, it can be purified directly. If the polypeptide is expressed as an associated product, it may require the partial or complete disruption of the host before purification. Examples of the procedures employed for the purification of polypeptides are: (i) immunoprecipitation or affinity chromatography with antibodies, (ii) affinity chromatography with a suitable ligand, (iii) other chromatography procedures such as gel filtration, ion exchange or high performance liquid chromatography or derivatives of any of the above, (iv) electrophoretic procedures like polyacrylamide gel electrophoresis, denaturating polyacrylamide gel electrophoresis, agarose gel electrophoresis and isoelectric focusing, (v) any other specific solubilization and/or purification techniques.

The present invention also relates to a substantially pure amelin polypeptide. In the present context, the term "substantially pure" is understood to mean that the polypeptide in question is substantially free from other components, e.g. other polypeptides or carbohydrates, which may result from the production and/or recovery of the polypeptide or otherwise be found together with the polypeptide. The purity of a protein may e.g. be assessed by SDS gel electrophoresis.

A high purity of the polypeptide of the invention may be advantageous when the polypeptide is to be used in a composition. Also due to its high purity, the substantially pure polypeptide may be used in a lower amount than a polypeptide of a conventional lower purity for most purposes.

In one aspect of the invention, the pure polypeptide may be obtained from a suitable cell line which expresses a polypeptide of the invention. Also, a polypeptide of the invention may be prepared by the well known methods of liquid or solid phase peptide synthesis utilizing the successive coupling of the individual amino acids of the polypeptide sequence. Alternatively, the polypeptide can be synthesized by the coupling of individual amino acids forming fragments of the polypeptide sequence which are later coupled so as to result in the desired polypeptide. These methods thus constitute another interesting aspect of the invention.

In a further aspect, the invention relates to a method of treating and/or preventing periodontal disease, the method comprising administering to a patient in need thereof a therapeutically or prophylactically effective amount of a polypeptide according to the invention. It is contemplated that the polypeptide of the invention will participate in cementum formation and thus improve the anchoring of the periodontal ligament.

The usage of amelin protein in the context of artificial local bone formation is indicated by the presence of amelin RNA sequences in bone forming cells: A size variant of the amelin RNA, fulifilling the criteria given above, was discovered in bone tissue from rat femur as well as calvaria by Northern blots. In situ hybridization with amelin probes localized this RNA to osteoblasts in association to growing bone. Also, rat calvarical cells which are forming bone in tissue culture were expressing the bone-variant of amelin RNA throughout the bone forming period (C. Brandsten, C. Christersson and T. Wurtz, unpublished).

The presence of amelin RNA sequences in natural and experimental bone forming systems indicates a role of the amelin protein in bone formation. It is conceivable that externally added amelin peptides accelerate or modulate bone formation both in vitro and in medical applications.

Furthermore, the invention relates to a method of repairing a lesion in a tooth, the method comprising administering to a patient in need thereof an effective amount of a polypeptide according to the invention in combination with appropriate filler material.

The invention also relates to a method of joining two bone elements and to a method of effectively incorporating an implant into a bone. In this context, the polypeptide may be administered in connection with a carrier as described in detail below. Moreover, the polypeptide of the invention could be used in a method of promoting or provoking the mineralization of hard tissue selected from the group consisting of bone, enamel, dentin and cementum.

Further, the invention also relates to a method of improving the biocompatibility of an implant device or a transcutaneous device e.g. in a similar manner as described in U.S. Pat. No. 4,578,079, the method comprising covering the implant device with an effective amount of a polypeptide according to the invention, thereby e.g. allowing muscle or ligament attachment to the implant.

Also, the invention relates to a method of anchoring epithelium to a hard tissue surface selected from the group consisting of enamel, dentin or cementum in connection with a tooth implant by administering the polypeptide of the invention. Moreover, the invention relates to a method of preventing growth of epithelium in connection with implantation of teeth, the method comprising administering to a patient in need thereof a prophylactically effective amount of a polypeptide according to the invention, e.g. thereby preventing epithelium from growing into the periodontal ligament.

A very important aspect of the invention relates to a composition comprising an amelin polypeptide and a physiologically acceptable excipient. The composition may comprise a purified recombinant polypeptide of the invention. Particularly, but not exclusively, the present invention relates to compositions suitable for topical application, e.g. application on the mucosal surfaces of the mouth.

Compositions of the invention suitable for topical administration may be liniments, gels, solutions, suspensions, pastes, sprays, powders, toothpastes, and mouthwashes.

The present invention comprises a toothpaste prepared by mixing the polypeptide of the invention with a toothpaste preparation, e.g. of the type commonly available as commercial toothpastes, which can be used on a regular basis for the prevention of e.g. periodontitis.

A toothpaste will usually contain polishing agents, surfactants, gelling agents and other excipients such as flavouring and colouring agents. The polishing agent may be selected from those which are currently employed for this purpose in dental preparations. Suitable examples are water-insoluble sodium or potassium metaphosphate, hydrated or anhydrous dicalcium phosphate, calcium pyrophosphate, zirconium silicate or mixtures thereof. Particularly useful polishing agents are various forms of silica. The polishing agent is generally finely divided, with a particle size smaller than 10 $\mu$m, for example 2–6 $\mu$m. The polishing agent may be employed in an amount of 10–99% a by weight of the toothpaste. Typically the toothpaste preparations will contain 20–75% of the polishing agent.

A suitable surfactant is normally included in the toothpaste preparations. The surfactant is typically a water-soluble non-soap synthetic organic detergent. Suitable detergents are the water-soluble salts of: higher fatty acid monoglyceride monosulphates (for example sodium hydrogenated coconut fatty acid monoglyceride monosulphate); higher alkyl sulphates (for example sodium lauryl sulphate); alkylarylsulphonates (for example sodium dodecylbenzenesulphonates); and higher alkyl sulphoacetates (for example sodium lauryl sulphoacetate). In addition, there may be employed saturated higher aliphatic acyl amides of lower aliphatic amino carboxylic acids having 12–16 carbon atoms in the acyl radical and in which the amino acid portion is derived from the lower aliphatic saturated monoaminocarboxylic acids having 2–6 carbon atoms, such as fatty acid amides of glycine, sarcosine, alanine, 3-aminopropanoic acid and valine, in particular the N-lauryl, myristoyl and palmitoyl sarcosinate compounds. Conventional non-ionic surfactants may also be included if desired.

The surface active materials are generally present in an amount of about 0.05–10%, typically about 0.5–5%, by weight of the toothpaste preparation.

Typically the liquids of the toothpaste will comprise mainly water, glycerol, sorbitol, propylene glycol or mixtures thereof. An advantageous mixture is water and glycerol, preferably with sorbitol. A gelling agent such as natural or synthetic gums and gum-like materials, e.g. Irish Moss or sodium carboxymethylcellulose, may be used. Other gums which may be used are gum tragacanth, polyvinyl-pyrrolidone and starch. They are usually used in an amount up to about 10%, typically about 0.5–5%, by weight of the toothpaste.

The pH of a toothpaste is substantially neutral, such as a pH of about 6–8. If desired, a small amount of a pH-regulating agent, e.g. a small amount of an acid such as citric acid or an alkaline material may be added.

The toothpaste may also contain other materials such as soluble saccharin, flavouring oils (e.g. oils of spearmint, peppermint, wintergreen), colouring or whitening agents (e.g. titanium dioxide), preservatives (e.g. sodium benzoate), emulsifying agents, silicones, alcohol, menthol and chlorophyll compounds (e.g. sodium copper chlorophyllin).

The content of the polypeptide of the invention in the toothpaste of the above type or types discussed below will normally be in the range of 1–20% by weight, calculated on the weight of the total toothpaste composition, such as in the range of 5–20% by weight, in particular about 10–20% by weight such as 12–18% by weight. The latter ranges are especially indicated for toothpastes which are used for treatment of gingivitis and periodontosis. It is, however, also interesting to provide toothpastes having a lower content of the polypeptide of the invention which will often predominantly be adapted for preventive or prophylactic purposes. For such purposes, a polypeptide content ranges from about 0.1 to about 5% by weight may be interesting.

A special type of toothpaste are toothpastes which are substantially clear gels. Such toothpastes may either contain no polishing agents at all or may contain the polishing agent in such finely divided form that the gels will still appear substantially clear. Such gel toothpaste types may either be used per se or may be combined with toothpastes containing polishing agents as discussed above.

The incorporation of the polypeptide of the invention a toothpaste preparation and other dental or oral preparations may be performed in many different ways. Often, it will be preferred to form a suspension of the polypeptide of the invention and combine the amelin suspension with the other preparation ingredients in paste form. Alternatively, dry amelin powder may be mixed with the other preparation components, either first with the dry preparation constituents and subsequently with liquid or semi-liquid preparation constituents, or amelin powder per se can be incorporated in an otherwise finished preparation. In general, it is preferred that the amelin powder is added together with the polishing material or dentifrice.

While the incorporation of amelin or other water-insoluble or sparingly water-soluble polypeptide analogues is best performed taking into consideration the physical and chemical properties of the polypeptide, considerations in toothpastes or dentifrices or other preparations discussed herein will normally be extremely simple and will ordinarily consist in the addition of the amelin polypeptide to the preparation or to constituents thereof in either dry, dissolved or suspended form.

The topical administration may be an administration onto or close to the parts of the body presenting the pathological changes in question, e.g. onto an exterior part of the body such as a mucosal surface of the mouth. The application may be a simple smearing on of the composition, or it may involve any device suited for enhancing the establishment of contact between the composition and the pathological lesions. The compositions may be impregnated or distributed onto pads, plasters, strips, gauze, sponge materials, cotton wool pieces, etc. Optionally, a form of injection of the composition into or near the lesions may be employed.

The topical compositions according to the present invention may comprise 1–80% of the active compound by weight, based on the total weight of the preparations, such as 0.001–25% w/w of the active compound, e.g., 0.1–10%, 0.5–5%, or 2–5%. More than one active compound may be incorporated in the composition; i.e. compositions comprising amelin protein in combination with other pharmaceutical compounds are also within the scope of the invention. The composition is conveniently applied 1–10 times a day, depending on the type, severity and localization of the lesions.

For topical application, the preparation may be formulated in accordance with conventional pharmaceutical practice, e.g. with pharmaceutical acceptable excipients conventionally used for topical applications in the mouth. The nature of the vehicle employed in the preparation of any particular composition will depend on the method intended for administration of that composition. Vehicles other than water that can be used in compositions can include solids or liquids such as emollients, solvents, humectants, thickeners and powders. It is contemplated that the composition according to the invention may consist of only the polypeptide, optionally in admixture with water, but the composition may also contain the polypeptide in combination with a carrier, diluent or a binder such as cellulose polymers, agar, alginate or gelatin which is acceptable for the purpose in question. For dental use it is convenient that the carrier or diluent is dentally acceptable. It is presently preferred to use a carrier comprising water-soluble polymers. Non-limiting examples of such polymers are sodium carboxy cellulose, microcrystalline cellulose, hydroxyethyl cellulose, hydroxypropyl cellulose, methyl cellulose, high molecular polyacrylic acid, sodium alginate, propylene glycol alginate, xanthan gum, guar gum, locust bean gum, modified starch, gelatin, pectin or combinations thereof. After incorporation of the active protein fraction, these water-soluble polymers may optionally be converted into gels or films, resulting in compositions which are easy to apply in view of their advantageous physical properties. The composition may optionally contain stabilizers or preservatives with the purpose of improving the storage stability. A suitable excipient will be an alginate, e.g. as described in EP 337967.

For topical application, the pH of the composition may in principle be within a very broad range such as 3–9. In a preferred embodiment of the invention, a pH of about 4 to 8 is preferred. Conventional buffering agents as described above may be used to obtain the desired pH.

The preparation of the invention may also contain other additives such as stabilizing agents, preservatives, solubilizers, chelating agents, gel forming agents, pH-regulators, anti-oxidants, etc. Furthermore, it may be advantageous to provide modified release preparations in which the active compound is incorporated into a polymer matrix, or nanoparticles, or liposomes or micelles, or adsorbed on ion exchange resins, or carried by a polymer.

Compositions may be formulated according to conventional pharmaceutical practice and may be:

Semisolid formulations: Gels, pastes, mixtures.

Liquid formulations: Solutions, suspensions, drenches, emulsions.

As indicated, a pharmaceutical composition of the invention may comprise a polypeptide of the invention itself or a functional derivative thereof, or a combination of such compounds. Examples of suitable functional derivatives include pharmaceutically acceptable salts, particularly those suitable for use in an oral environment. Examples include pharmaceutically acceptable salts of the amino function, for example salts with acids yielding anions which are pharmaceutically acceptable, particularly in an oral environment. Examples include phosphates, sulphates, nitrate, iodide, bromide, chloride, borate as well as anions derived from carboxylic acids including acetate, benzoate, stearate, etc. Other derivatives of the amino function include amides, imides, ureas, carbamates, etc.

Other suitable derivatives include derivatives of the carboxyl group of a polypeptide of the invention, including salts, esters and amides. Examples include salts with pharmaceutically acceptable cations, e.g. lithium, sodium, potassium, magnesium, calcium, zinc, aluminium, ferric, ferrous, ammonium and lower($C_{1-6}$)-alkylammonium salts. Esters include lower alkyl esters.

The invention will be further described by means of a number of working examples which should not be construed as limiting the scope of this application.

Conventional methods and kits were used unless otherwise indicated. The kits were used in accordance with the instructions given by the respective supplier. Methodological steps as well as reagents which are not described or mentioned here are explained in: Current Protocols in Molecular Biology, by F. M. Ausubel, R. Brent, R. E. Kingston, D. D. Moore, J. G. Seidman, J. A. Smith and K. Struhl; John Wiley, New York (1994). All literature citations are expressly incorporated herein by reference.

EXAMPLES

Example 1

Isolation of RNA

Three dissected growing molars from 4 day or 7 day old Sprague-Dawley rats (B&K Universal, Sollentuna, Sweden) were homogenized in a glass—glass homogenizer in 500 l of 4M guanidinium isothiocyanate, 80 mM EDTA (Chomczynski & Sacchi, 1987), using a commercial kit (Promega Biotech, RNAgents Total RNA Isolation System). This was followed by phenolchloroform extraction and two isopropanol precipitations. RNA was dissolved in 0.2×SET buffer (0.2% sodium dodecyl sulphate, 4 mM Tris-Cl pH 7.5, 2 mM EDTA) and the concentration was determined by optical density measurements.

Example 2

Preparation of cDNA Library

Poly-A containing RNA (mRNA) was selected with the help of oligo-dT, bound to silicate-resin (Quiagen Oligotex mRNA Midi kit). Reverse transcription was primed at the poly-A end, and double-stranded, methylated cDNA was ligated to lambda ZAP vector arms and packaged into phage particles (Stratagen ZAP-cDNA Cloning Kit). After amplification and plating, phage strains containing frequently expressed sequences were selected by hybridization with a total DIG labelled cDNA (see below). Phages from positive plaques were isolated and converted to plasmids by superinfection of lambda ZAP-infected *Escherichia coli* SOLR cells with ExAssist helper phage. To obtain a better representation of the 5' ends, a library with a cDNA was also constructed and primed at random sites (Stratagen Random Unidirectional Linker-Primer). Inserts giving positive in situ hybridization signals on matrix forming cells were sequenced using cycle sequencing with Taq-polymerase, fluorescent terminators and a semiautomatic sequence detection system (Applied Biosystems, Taq DyeDeoxy Terminator Cycle Sequencing Kit). Sequences were analysed with the Wisconsin program set (Genetics Computer Group, Inc.) and with DNAid (Frédéric Dardel, fred@botrytis.polytechnique.fr).

Example 3

Library Screening

Lambda phages of a tooth cDNA library ($2 \times 10^6$ clones) from first and second molars of seven day old rats were plated, and plaques were adsorbed to nitrocellulose membranes (Schleicher and Schull). Replica filters were hybridized to 10 ng/ml cDNA or to collagen- and amelogenin oligonucleotides. Hybridization was carried out at 54° C. for 15 hours, and the filters were washed and developed (Boehringer Mannheim, The DIG System). Phages containing amelogenin, collagen or remaining frequently expressed sequences were re-cloned twice and converted to Bluescript plasmids by in vivo excision, accomplished by superinfection with the ExAssist helper phage (Stratagen).

Example 4

Preparation of Probes for Hybridization Assays cDNA probes for library screening were produced from poly-A enriched RNA with reverse transcriptase (Promega Biotech, Reverse Transcription System), using a nucleotide concentration of 0.25 mM supplemented with digoxygenin (DIG)-dUTP (Boehringer Mannheim) to 0.1 mM.

RNA probes complementary to the mRNA sequences were synthesized by in vitro transcription by phage T7 or T3 RNA polymerase (Promega Riboprobe Gemini II Core System, Melton et al., 1984), in the presence of DIG-modified UTP (Boehringer Mannheim). The DNA templates containing amelin (1700 bp) were Bluescript plasmids, derived from λ bacteriophages by in vivo excision. Furthermore, amelogenin (700 bp) and collagen type I (850 bp) sequences were obtained by restriction enzyme cleavage of Bluescript SK plasmids. Probes for quantitative RNA determinations were labelled with [$^{35}$S] instead of DIG.

The collagen-specific oligonucleotide had the sequence 5'-CATGTAGGCAATGCTGTTCTT GCAGTGGTAGGT GATGTTCTGGGAGGC-3' (SEQ ID NO:8) (Yamada et al., 1983), and the amelogenin-specific oligonucleotide was 5'-ATCCACTTCTTCCCGCTTGGTCTTGTCTGTCGCT GGCCAAGCTTC-3' (SEQ ID NO: 9) (Lau et al., 1992). Probes were prepared by 3' labelling with DIG-modified ddUTP by a terminal transferase reaction according to a Boehringer protocol.

Example 5

Northern Blotting

For Northern blot analysis, 15 mg of total RNA per well of 2 cm width were heat denatured in the presence of 50% formamide and electrophoresed in an agarose gel with 2.2M formaldehyde, 0.02 M N-morpholinopropane sulphonic acid, 0.05 M sodium acetate, 1 mM EDTA (Lehrach et al., 1977). RNA was transferred overnight to a nylon membrane (Pall Biodyne B Transfer Membrane) in 20×SSC (3 M NaCl, 0.3 M sodium citrate). The membranes were crosslinked with UV light and cut in strips. Individual strips were prehybridized for 1 hour at 68° C. in 50% formamide, 5×SSC, 2% blocking reagent (Boehringer Mannheim), 0.1% N-lauroyl-sarcosine, 0.02% sodium dodecyl sulphate (SDS) and subsequently hybridized overnight under the same conditions, following the addition of the DIG labelled cRNA probe at 100 ng/ml. Membranes were then washed 2 times for 5 minutes with 2×SSC, 0.1% SDS at room temperature and 2 times for 15 minutes at 68° C. with 0.1×SSC, 0.1% SDS. The presence of DIG labelled RNA was developed via phosphatase-coupled anti DIG antibody fragments (Boehringer Mannheim, The DIG System).

Example 6

Solution Hybridization

RNA from dissected molars was hybridized to of $^{35}$S-UTP labelled complementary RNA probes in excess (Mathews et al., 1989). Reactions of 40 l of 0.6 M NaCl, 4 mM EDTA, 10 mM dithiothreitol (DTT), 0.1% SDS, 30 mM Tris-HCl, pH 7.5 and 25% (v/v) formamide contained 20,000 cpm probe and different amounts of total RNA. The mixture was covered by paraffin oil, incubated overnight at 70° C., diluted with 1 ml of RNase solution (40 g of RNase A, 2 g of RNase Ti, Boehringer-Mannheim, 100 g of salmon testes DNA, Sigma Chemical Co.) and digested for 1 hour at 37° C. RNase resistant double-stranded RNA was precipitated by 100 l of trichloroacetic acid (6M), collected on glass-fibre filters (Whatman GF/C) and analysed in a Wallac 1409 liquid scintillation counter. Standard curves, where the probes were hybridized to known concentrations of in vitro synthesized mRNA sequences, were used to relate the radioactivity to the amount of hybridizing sequences in the test-RNA.

Example 7

In situ Hybridization

Upper jaws from Sprague Dawley rats of four days of age were fixed with 4% paraformaldehyde in PBS (137 mM NaCl, 2.7 mM KCl, 4.3 mM $Na_2HPO_4$, 1.4 mM $KH_2PO_4$) for 24 hours at 4° C., dehydrated and embedded in paraffin. Sections of 7 μm thickness were mounted on vectabond-coated (Vector) glass slides. After the removal of the paraffin with xylene, the specimens were treated with proteinase K (20 μg/ml) for 30 minutes at 37° C., post-fixed with 4% formaldehyde for 5 minutes, treated with triethanolamine and acetic anhydride (2.66 ml of triethanolamine in 200 ml of water; 0.5 ml of acetic anhydride was added together with the slides) and immersed in 2×SSC, 50% formamide at 42° C. for 60 minutes. The specimens were overlayered with 20 μl of 0.3 M NaCl, 10 mM Tris-Cl pH 8.0, 1 mM EDTA, Denhardt reagent (Watkins, 1994), 0.1 g/l dextran sulphate, 50% formamide, containing 0.5 ng/μl RNA probe. The specimens were covered with a coverglass, and the slides were kept in a humid chamber overnight at 42° C., washed once with 4×SSC, three times for 10 minutes with 2×SSC and three times for 10 minutes with 0.1×SSC at room temperature. The presence of DIG labelled RNA probe was revealed through phosphatase-coupled anti-DIG antibody fragments (Boehringer Mannheim protocol). No staining of the specimen due to endogenous phosphatase activity was observed.

Example 8

Sequential Expression of the Amelin Gene

Using the in situ hybridization technique as described in example 7 the cellular expression of the amelin gene was examined in rats of either 20 or 25 days of age. Sections from upper jaw were prepared and hybridized to an amelin RNA probe. At both developmental stages it was found that the amelin gene was expressed in epithelial cells adjacent to the peripheral surface of newly deposited dentin in the root cementum-forming end as well as in cells embedded in cellular cementum in molars. Amelin gene expression was further localized to secreting ameloblasts as well as to the epithelial root sheath. In addition, incisors from 20 day old rats showed evidence for amelin expression in mantle dentine-secreting odontoblasts before its expression was switched over to differentiating ameloblasts. In combination, these results suggest a putative function of amelin in epithelial-mesenchymal interactions during the cytodifferentiation of odontoblasts and ameloblasts and that amelin might be one of the key proteins coupled to the process of cementogenesis.

Example 9

Construction of the Amelin 1 Full-Length cDNA Sequence

Amelin 1 sequence was derived from a number of overlapping clones found in the rat tooth cDNA library. None of the clones covered a full length of the amelin 1 mRNA. In order to express amelin 1 it was necessary to join the overlapping clones into a full-length sequence. The longest available clone A6 and the overlapping clone R6.8 were used for the generation of full length sequence. Clone A6 comprises a cDNA sequence corresponding to nucleotides 231–1940 of SEQ ID NO:1 and clone A6.8 comprises a cDNA sequence corresponding to nucleotides 1–421. In the following examples, all nucleotide positions refer to the sequence comprised in SEQ ID NO:1. A suitable restriction site was XbaI site (nucleotides 296–301). However, since XbaI is contained in the proximal part of the multiple cloning site of the vector, both orientations of the insert would be expected. Several clones were digested with HindIII and this enabled selection of the correct orientation of the insert. The junctions between vector and insert were sequenced, confirming that the amelin 1 cDNA comprises the sequence from nucleotide 1 to nucleotide 1940.

Example 10

Expression of Amelin Fragments Using the Vector pTrxFus

Cloning of part of the amelin coding sequence into pTrxFus (ThioFusion Expression System, Invitrogen) generated expression of a truncated amelin protein fused to thioredoxin. In one experiment, amelin 1 cDNA was digested with KpnI (nucleotide 602) and PstI (nucleotide 1093) and the resulting fragment was cloned into pTrxFus digested with KpnI and PstI. In another example, amelin 1 cDNA was digested with KpnI (nucleotide 602) and ClaT (nucleotide 1543) and the resulting fragment was cloned into pTrxFus digested with KpnI and AccI. Expression was confirmed by polyacrylamide gelelectrophoresis of proteins extracted from bacteria.

Example 11

Construction of pTrx6His

The original pTrxFus vector was digested with BspMI and PstI and purified by gel electrophoresis. The linearized vector was ligated to an insert created from annealing two complementary oligonucleotides:

(SEQ ID NO:5)
5'-GGTCGTCATC ACCATCACCA TCACTA-3'

(SEQ ID NO:6)
5'-CGATTAGTGA TGGTGATGGT GATGACGACC TGCA-3'

The vector generated by this ligation, pTrx6His, contains the 6 x His affinity tag and a stop codon immediately downstream of PstI and does not alter the multiple cloning site. Two amino acids were introduced between PstI and the 6 x His affinity tag: glycine (to maintain PstI and to facilitate a switch to an appropriate reading frame) and arginine (to facilitate removal of the 6 x His tag by carboxypeptidase A). pTrx6His was confirmed by sequencing across the annealed, cloned oligonucleotides.

Example 12

Expression of Amelin Fragments Using the Vector pTrx6His

Cloning of part of the amelin coding sequence into pTrx6His generated expression of a fusion of thioredoxin to a truncated amelin protein comprising the 6 His affinity tag in the C terminal end. In one experiment, amelin 1 cDNA was digested with KpnI (nucleotide 602) and PstI (nucleotide 1093) and the resulting fragment was cloned into pTrx6His digested with KpnI and PstI. In another example, amelin 1 cDNA was digested with KpnI (nucleotide 602) and Nsiir (nucleotide 1297) and the resulting fragment was cloned into pTrx6His digested with KpnI and PstI. Expression was confirmed by polyacrylamide gelelectrophoresis of proteins extracted from bacteria.

Example 13
Construction of pTrxAme6His

The vector pTrxAme6His was constructed by cloning a PCR generated fragment obtained by using custom designed oligonucleotides and amelin 1 cDNA as template. The proximal primer hybridized to the C terminal part of the signal sequence (nucleotides 143–173) and comprised the recognition site for BamHI. The distal primer annealed to nucleotides 1524–1550 downstream of the native amelin 1 stop codon. The PCR fragment was digested with BamHI and NsiI (nucleotide 1297) and cloned into pTrx6His digested with BamMI and PstI, generating pTrxAme6his. The expressible gene product comprises bacterial thioredoxin with several connecting amino acids, as dictated by the structure of the pTrxFus multiple cloning site, followed by the amelin 1 amino acid sequence, starting from the valine (nucleotides 155–157) and ending at alanine (nucleotides 1295–1297), fused to glycine, arginine and the 6 His affinity tag. This construct generated an efficient overexpression and was used for the production and purification of recombinant amelin fusion protein, which was subsequently used for theraising of antibodies.

Example 14
Production of Recombinant Full Length Amelin Fusion Protein pTrxAme6His was used for the production of full length recombinant amelin as a fusion protein with bacterial thioredoxin at the N-terminus and 6 His affinity tag at the C-terminus.

*Escherichia coli* GI698 cells contaning pTrxAme6His were grown at 30° C. and induced by tryptophan (100 µg/ml) as described in the ThioFusion Expression System instruction manual (Invitrogen). Cells were harvested by centrifugation and resuspended in 3 volumes per gramme of wet weight of 50 mM Na-phosphate, pH 8.0, 100 mM NaCl, 20 mM imidazole, 0.01 mM EDTA, 1 mM phenylmethylsulfonyl fluoride (PMSF). After sonication (3×10 second bursts), the lysate was frozen in a dry ice-ethanol bath and quickly thawed at 37° C. Three sonication-freeze-thaw cycles were performed. The lysate was then treated with RNase A (10 µg/ml) and DNase I (5 µg/ml) at 4° C. for 15 minutes.

After centrifugation at 12,000× g for 30 minutes, the supernatant was applied on a Ni-NTA (Qiagen) column equilibrated with 50 mM Na-phosphate buffer, pH 8.0, 100 mM NaCl, 1 mM PMSF. The column was extensively washed with the same buffer containing 20 mM imidazole and eluted with 200 mM imidazole. Alternatively, a Talon Metal Affinity Resin (Clontech) column was used under similar conditions, but the column was washed with 5 mM imidazole and eluted with 90 mM imidazole.

The amelin-thioredoxin fusion protein could be further purified on the column of SEPHAROSE 4B agarose coupled with thioredoxin antibody, equilibrated in 10 mM Tris-Cl buffer, pH 8.0, 1 mM EDTA, 0.14 mM NaCl, 0.5% TRITON X-100 detergent. After washing the column with the same buffer, the pure recombinant protein was eluted with 0.1 M acetic acid+formic acid, pH 2.0. Fractions were neutralized immediately with 0.25 volume of 1 M Tris-Cl buffer, pH 9.0.

The recombinant amelin-thioredoxin fusion protein coupled to Sepharose 4B was used for affinity purification of rabbit amelin antibody. The antibody against bacterial thioredoxin did not cross-react with eukaryotic thioredoxin.

Example 15
Preparation of Amelin Antibodies

Rabbits were boosted with the recombinant thioredoxin-amelin fusion protein. The IgG fraction from rabbit antiserum was prepared by precipitation with ammonium sulfate to 33% saturation. After centrifugation, the pellet was washed with 33% saturated ammonium sulfate and dissolved in phosphate buffered saline (PBS). The IgG solution was then dialyzed for 48 hours at 4° C. against three changes of PBS.

The dialyzed IgG fraction was directly applied to the column of Sepharose 4B coupled with the recombinant thioredoxin-amelin fusion protein. The column was pre-equilibrated and washed with PBS. Polyclonal thioredoxin-amelin antibodies were eluted with glycine-Cl buffer, pH 2.3, 0.15 M NaCl and neutralized with 0.25 volume of 0.5 M phosphate buffer, pH 8.0. The antibody gave positive signals on Western blots with both recombinant thioredoxin-amelin and amelin in the crude extract from rat teeth. There was no cross-reactivity with eukaryotic thioredoxin.

Example 16
Purification of Amelin from Rat Teeth

Sprague-Dawley rats at an age of 6 days were killed by decapitation and the tooth germs of maxillary first and second molars were collected. The dental pulp of each tooth germ was dissected and removed.

Pulpless tooth germs were suspended in 10 volumes of 50 mM sodium carbonate-sodium bicarbonate buffer, pH 10.5, 5 mM EDTA, containing proteinase and phosphatase inhibitors (50 mM aminocapronic acid, 5 mM benzamidine, 1 mM hydroxymercuribenzoic acid, 1 mM phenylmethylsulfonyl fluoride and 1 mM levarmizole), homogenized using a Polytron homogenizer for 30 seconds at half speed and centrifuged for 15 min at 10,000× g. The extraction procedure was repeated three times.

After centrifugation, solid ammonium sulfate was added to 29% saturation to the supernatant at 4° C. The precipitate was removed by centrifugation and additional solid ammonium sulfate was added up to 80% saturation to the supernatant. After centrifugation, the precipitate was dissolved in 50 mM carbonate-bicarbonate buffer, pH 10.5, 1 mM EDTA, 75 mM NaCl, containing the above-mentioned inhibitors, and desalted on an Econo-Column (Bio-Rad) equilibrated with the same buffer.

The desalted sample was then chromatographed on a Mono Q column on an FPLC system (Pharmacia) using a gradient of 0–0.5 M NaCl in 50 mM Tris-Cl buffer, pH 8.0, 1 mM EDTA. Amelin was eluted at 150 mM NaCl. Amelin-containing fractions, detected by immunoblotting, were pooled and optionally concentrated on a Centricon-30 microconcentrator (Amicon).

Amelin was further purified to homogeneity by affinity chromatography on Sepharose 4B coupled with antigen affinity purified amelin antibodies. Pooled amelin eluate from the FPLC Mono Q column was directly applied on a Sepharose-anti-amelin column equilibrated with 10 mM Tris-Cl buffer, pH 8.0, 0.14 mM NaCl, 0.5% Triton X-100. The column was first washed with the same buffer followed by a wash with 50 mM Tris-Cl buffer, pH 9.0, 0.1% Triton X-100, 0.5 M NaCl. Finally, the pure amelin was eluted with 50 mM triethanolamine, pH 11.3, 0.1% Triton X-100, 0.15 M NaCl into tubes contaning 0.2 volume of 1 M Tris-Cl buffer, pH 6.7. The purity of the protein was established by means of Western blotting and SDS gel electrophoresis using the silver staining technique.

REFERENCES

Ausubel, F. M., Brent, R., Kingston, R. E., Moore, D. D., Seidman, J. G., Smith, J. A. & Struhl, K. (1994). Current protocols in Molecular Biology. John Wiley, New York.

Chomczynski, P. & Sacchi, N. (1987). Single Step Method of RNA Isolation by Acid Guanidinium Thiocyanate-Phenol-Chloroform Extraction. Anal. Biochem. 162, 385–293.

Deutsch, D., Palmon, A., Fisher, L. W., Kolodny, N., Termine, J. D. & Young, M. F. (1991). Sequencing of Bovine Enamelin ("Tuftelin") a Novel Acidic Enamel Protein. J. Biol. Chem. 266, 16021–16028.

Hopp, T. P. & Woods, K. R. (1981). Prediction of protein antigenic determinants from amino acid sequences. Proc. Natl. Acad. Sci. U.S.A. 78, 3824–3828.

Lau, E. C., Simmer, J. P., BringasJr, P., Hsu, D. D.-J., Hu, C.-C., Zeichner-David, M., Thiemann, F., Snead, M. L., Slavkin, H. C. & Fincham, A. G. (1992). Alternative Splicing of the Mouse Amelogenin Primary RNA Transcript Contributes to Amelogenin Heterogeneiety. Biochem. Biophys. Res. Commun. 188, 1253–1260.

Leader, D. P. (1979). Amino acid sequences of signal peptides. Trends Biochem. Sci. 4, 205–208.

Lehrach, H., Diamond, D., Wozney, J. M. & Boedtker, H. (1977). RNA Molecular Weight Determinations by Gel Electrophoresis under Denaturing Conditions: a Critical Reexamination. Biochemistry 16, 4743–4751.

Mathews, L. S., Enberg, B. & Norstedt, G. (1989). Regulation of rat growth hormone receptor gene expression. J. Biol. Chem. 264, 9905–9910.

Matsuki, Y., Nakashima, M., Amizuka, N., Warshawsly, H., Goltzman, D., Yamada, K. M., and Yamada, Y. (1995). A compilation of partial sequences of randomly selected cDNA clones from the rat incisor. J, Dent. Res. 74, 307–312.

Melton, D. A., Krieg, P. A., Rebagliati, M. R., Maniatis, T., Zinn, K. & Green, M. R. (1984). Efficient in vitro synthesis of biologically active RNA and RNA hybridization probes from plasmids containing a bacteriopjage SP6 promotor. Nucleic Acids Res. 12, 7035–7056.

Robinson, C., Kirkham, J. & Hallsworth, A. S. (1988). Volume Distribution and Concentration of Protein, Mineral and Water in Developing Bovine Teeth. Archs. Oral Biol. 33, 159–162.

Simmer, J. P., Lau, E. C., Hu, C. C., Aoba, T., Lacey, M., Nelson, D., Zeichner-David, M., Snead, M. L., Slavkin, H. C. & Fincham, A. G. (1994). Isolation and Characterization of a Mouse Amelogenin Expressed in *Escherichia coli*. Calcif. Tissue Int. 54, 312–319.

Staatz, W. D., Fok, K. F., Zutter, M. M., Adams, S. P., Rodriguez, B. A. & Santoro, S. A. (1991). Identification of a Tetrapeptide Recognition Sequence for the alpha2beta1 Integrin in Collagen. J. Biol. Chem. 266, 7363–7367.

Strawich, E. & Glimcher, M. J. (1990). Tooth 'enameling' identified mainly as serum proteins. Eur. J. Biochem. 191, 47–56.

Termine, J. D., Belcourt, A. B., Christner, P. J., Conn, K. M. & Nylen, M. U. (1980). Properties of Dissociatively Extracted Fetal Tooth Matrix Proteins. J. Biol. Chem. 255, 9760–9768.

Uchida, T., Fukae, M., Tanabe, T., Yamakoshi, Y., Satoda, T., Murakami, C., Takahashi, O. & Shimizu, M. (1995). Immunochemical and immunocytochemical study of a 15 kDa non-amelogenin and related proteins in the porcine immature enamel: Proposal of a new group of enamel proteins "sheath proteins". Biomed. Res. 16, 131–140.

Wilkinson, D. L. & Harrison, R. G. (1991). Predicting the solubility of recombinant proteins in *Escherichia coli*. Biotechnology 9, 443–448.

Watkins, S. (1994). In situ Hybridization and Immunohistochemistry. In Current Protocols in Molecular Biology. Ausubel, F. M., Brent, R., Kingston, R. E., Moore, D. D., Seidman, J. G., Smith, J. A. & Struhl, K. John Wiley, New York.

Yamada, Y. & Kleinman, H. K. (1992). Functional domains of cell adhesion molecules. Curr. Opin. Cell Biol. 4, 819–823.

Yamada, Y., Kühn, K. & deCrombrugghe, B. (1983). A conserved nucleotide sequence, coding for a segment of the C-propeptide, is found at the same location in different collagen genes. Nucl. Acids Res. 11, 2733–2744.

WO 89/08441 (Biora A. B.; published Sep. 21, 1989)

We claim:

1. An at least partially purified nucleic acid encoding a polypeptide which comprises an amino acid subsequence S having a length of 20 amino acids, said subsequence S comprising at least one sequence element selected from the group consisting of the tetrapeptides DGEA (Asp-Gly-Glu-Ala), VTKG (Val-Thr-Lys-Gly), EKGE (Glu-Lys-Gly-Glu) and DKGE (Asp-Lys-Gly-Glu), which subsequence S has a percentage sequence identity of at least 80% with at least one 20 amino acid reference subsequence of a reference sequence selected from the group consisting of (a) the amino acid sequence shown in SEQ ID NO:2, and (b) the amino acid sequence shown in SEQ ID:4, the reference subsequence likewise comprising said sequence element, where said polypeptide exhibits at least one of the following activities when administered in an effective amount to a subject:

(i) binds to enamel;
(ii) binds to ameloblasts;
(iii) mediates contact between the enamel and the surface of a cell;
(iv) competitively inhibits contact between an extracellular matrix protein and the surface of a cell;
(v) promotes mineralization of bone, enamel, dentin or cementum; or
(vi) promotes formation of the enamel matrix or of hard tissues of mesenchymal origin.

2. The nucleic acid of claim 1 where said polypeptide comprises the amino acid sequence SEQ ID NO:2.

3. The nucleic acid claim 1 where said polypeptide comprises the amino acid sequence SEQ ID NO:4.

4. The nucleic acid of claim 1 where said polypeptide has activity (i).

5. The nucleic acid of claim 1 where said polypeptide has activity (ii).

6. The nucleic acid of claim 1 where said polypeptide has activity (iii).

7. The nucleic acid of claim 1 where said polypeptide has activity (iv).

8. The nucleic acid of claim 1 where said polypeptide has activity (v).

9. The nucleic acid of claim 1 where said polypeptide has activity (vi).

10. The nucleic acid of claim 1, said subsequence S comprising at least one sequence element selected from the group consisting of the tetrapeptides DGEA (Asp-Gly-Glu-Ala), VTKG (Val-Thr-Lys-Gly), EKGE (Glu-Lys-Gly-Glu) and DKGE (Asp-Lys-Gly-Glu).

11. The nucleic acid of claim 8 where said polypeptide promotes mineralization of teeth.

12. The nucleic acid of claim 1 where said polypeptide comprises the amino acid sequence 1–407 in SEQ ID NO:2 except for the changes of Gln33 to Arg, Ala36 to Gly, Ala175 to Gly, Ala 239 to Gly and Ala295 to Pro.

13. The nucleic acid of claim 1 where said polypeptide comprises the amino acid sequence 1–324 in SEQ ID NO:4 except for the changes of Ala92 to Gly, Ala156 to Gly and Ala212 to Pro.

14. An at least partially purified nucleic acid, at least 18 nucleotides long, encoding a polypeptide, said nucleic acid being (I) a nucleic acid whose coding strand hybridizes with the noncoding strand of (a) a nucleic acid having the coding strand nucleotide sequence shown in SEQ ID NO: 1, or (b) a nucleic acid having the coding strand nucleotide sequence shown in SEQ ID NO:3 under stringent conditions, said conditions being 5 mM monovalent ions (0.1×SSC), neutral pH and 65° C., or (II) a nucleic acid which encodes the same polypeptide as a nucleic acid of (I) above, where said polypeptide exhibits at least one of the following activities when administered in an effective amount to a subject:

(i) binds to enamel;
(ii) binds to ameloblasts;
(iii) mediates contact between the enamel and the surface of a cell;
(iv) competitively inhibits contact between an extracellular matrix protein and the surface of a cell;
(v) promotes mineralization of bone, enamel, dentin or cementum; or
(vi) promotes formation of the enamel matrix or of hard tissues of mesenchymal origin.

15. The nucleic acid of claim 14 where said polypeptide has activity (i).

16. The nucleic acid of claim 14 where said polypeptide has activity (ii).

17. The nucleic acid of claim 14 where said polypeptide has activity (iii).

18. The nucleic acid of claim 14 where said polypeptide has activity (iv).

19. The nucleic acid of claim 14 where said polypeptide has activity (v).

20. The nucleic acid of claim 14 where said polypeptide has activity (vi).

21. The nucleic acid of claim 14 where said polypeptide comprises at least one sequence element selected from the group consisting of the tetrapeptides DGEA (Asp-Gly-Glu-Ala), VTKG (Val-Thr-Lys-Gly), EKGE (Glu-Lys-Gly-Glu) and DKGE (Asp-Lys-Gly-Glu).

22. The nucleic acid of claim 14 where said nucleic acid is at least 21 nucleotides long.

23. The nucleic acid of claim 14 where said nucleic acid is at least 48 nucleotides long.

24. The nucleic acid of claim 14 where said nucleic acid is at least 75 nucleotides long.

25. The nucleic acid of claim 14 where said nucleic acid is at least 99 nucleotides long.

26. The nucleic acid of claim 14 where the polypeptide is encoded by (I).

27. The nucleic acid of claim 26 where (I) hybridizes with (a).

28. The nucleic acid of claim 26 where (I) hybridizes with (b).

29. An at least partially purified nucleic acid encoding a polypeptide which is at least six amino acids long, and which is bound by an antibody which also binds amelin-1, having the amino acid sequence of SEQ ID NO:2, or amelin-2, having the amino acid sequence of SEQ ID NO:4, said polypeptide mediating contact between enamel and cell surfaces.

30. An at least partially purified nucleic acid encoding a polypeptide comprises at least one sequence element selected from the group consisting of the tetrapeptides DGEA (Asp-Gly-Glu-Ala), VTKG (Val-Thr-Lys-Gly), EKGE (Glu-Lys-Gly-Glu) and DKGE (Asp-Lys-Gly-Glu), where said polypeptide has a percentage amino acid sequence identity of at least 80% with SEQ ID NO:2 or SEQ ID NO:4, and where said polypeptide exhibits at least one of the following activities when administered in an effective amount to a subject:

(i) binds to enamel;

(ii) binds to ameloblasts;

(iii) mediates contact between the enamel and the surface of a cell;

(iv) competitively inhibits contact between an extracellular matrix protein and the surface of a cell;

(v) promotes mineralization of bone, enamel, dentin or cementum; or (vi) promotes formation of the enamel matrix or of hard tissues of mesenchymal origin.

31. The nucleic acid of claim 30 where said polypeptide has activity (i).

32. The nucleic acid of claim 30 where said polypeptide has activity (ii).

33. The nucleic acid of claim 30 where said polypeptide has activity (iii).

34. The nucleic acid of claim 30 where said polypeptide has activity (iv).

35. The nucleic acid of claim 30 where said polypeptide has activity (v).

36. The nucleic acid of claim 30 where said polypeptide has activity (vi).

37. The nucleic acid of claim 30 where said percentage identity is at least 85%.

38. The nucleic acid of claim 30 where said percentage identity is at least 90%.

39. The nucleic acid of claim 30 where said polypeptide comprises at least one sequence element selected from the group consisting of the tetrapeptides DGEA (Asp-Gly-Glu-Ala), VTKG (Val-Thr-Lys-Gly), EKGE (Glu-Lys-Gly-Glu) and DKGE (Asp-Lys-Gly-Glu).

40. The nucleic acid of claim 30 where said sequences are aligned, and percentage identity calculated, using the Wisconsin sequence analysis program set (Genetics Computer Group, Inc.), and the default parameter settings therefor, as they existed in the version of said program set which was current on Oct. 14, 1995.

41. The nucleic acid of claim 14 where said polypeptide has a percentage amino acid sequence identity of at least 80% with SEQ ID NO:2 or SEQ ID NO:4.

42. The nucleic acid of claim 1 where said polypeptide has a percentage amino acid sequence identity of at least 80% with SEQ ID NO:2 or SEQ ID NO:4.

43. The nucleic acid of claim 1 where said nucleic acid is (I) a nucleic acid whose coding strand hybridizes with the noncoding strand of (a) a nucleic acid having the coding strand nucleotide sequence shown in SEQ ID NO:1, or (b) a nucleic acid having the coding strand nucleotide sequence shown in SEQ ID NO:3 under stringent conditions, said conditions being 5 mM monovalent ions (0.1×SSC), neutral pH and 65° C., or (II) a nucleic acid which encodes the same polypeptide as a nucleic acid of (I) above.

44. The nucleic acid of claim 43 where said polypeptide has a percentage amino acid sequence identity of at least 80% with SEQ ID NO:2 or SEQ ID NO:4.

45. The nucleic acid of claim 14, in labeled form.

46. A replicable expression vector which carries and is capable of mediating the expression of a nucleic acid as defined in claim 1.

47. A cell comprising an expression vector according to claim 46.

48. A method of producing a polypeptide comprising cultivating a cell according to claim 1 under conditions suitable for expressing the polypeptide, and recovering the polypeptide.

49. A method of producing a polypeptide comprising cultivating a cell comprising an expression vector which carries and is capable of mediating the expression of a nucleic acid as defined in claim 14, under conditions suitable for expressing the polypeptide, and recovering the polypeptide.

50. A method of producing a polypeptide comprising cultivating a cell comprising an expression vector which carries and is capable of mediating the expression of a nucleic acid as defined in claim 30, under conditions suitable for expressing the polypeptide, and recovering the polypeptide.

51. A method of repairing a lesion in a tooth, the method comprising administering to a patient in need thereof an effective amount of a polypeptide encoded by a nucleic acid of claim 8.

52. A method of joining two bond elements, the method comprising administering to a patient in need thereof an effective amount of a polypeptide encoded by a nucleic acid of claim 8.

53. A method of promoting or provoking the mineralization of hard tissue selected from the group consisting of bond, enamel, dentin and cementum, the method comprising administering to a patient in need thereof an effective amount of a polypeptide according to claim 8.

* * * * *